United States Patent
Muramatsu et al.

(10) Patent No.: US 6,923,818 B2
(45) Date of Patent: Aug. 2, 2005

(54) APPARATUS FOR LIGATING LIVING TISSUES

(75) Inventors: Junichi Muramatsu, Akiruno (JP); Tsukasa Kobayashi, Hachioji (JP)

(73) Assignee: Olympus Corporation, Tokyo (JP)

( * ) Notice: Subject to any disclaimer, the term of this patent is extended or adjusted under 35 U.S.C. 154(b) by 455 days.

(21) Appl. No.: 10/102,127

(22) Filed: Mar. 20, 2002

(65) Prior Publication Data

US 2002/0138083 A1 Sep. 26, 2002

(30) Foreign Application Priority Data

Mar. 26, 2001 (JP) .......................................... 2001-088382

(51) Int. Cl.⁷ .............................................. A61B 17/10
(52) U.S. Cl. ........................ 606/142; 606/139; 606/143
(58) Field of Search ................................ 606/142, 143, 606/151, 157, 158; 600/104; 604/22; 227/175.1

(56) References Cited

U.S. PATENT DOCUMENTS 5,242,456 A    9/1993  Nash et al.
5,788,716 A *  8/1998  Kobren et al. ............... 606/142
6,352,503 B1 * 3/2002  Matsui et al. ................ 600/104

FOREIGN PATENT DOCUMENTS

| JP | 63-267345 | 11/1988 |
| JP | 2-6011 | 1/1990 |
| JP | 8-196623 | 8/1996 |

* cited by examiner

Primary Examiner—Julian W. Woo
(74) Attorney, Agent, or Firm—Scully, Scott, Murphy & Presser

(57) ABSTRACT

An apparatus for ligating living tissues comprises an introducing tube capable of being inserted into a living body cavity, a manipulating wire movably inserted into the introducing tube, and clips for ligating living tissues, the clips being arranged in the introducing tube. The introducing tube has a plurality of tube channels. A plurality of clips are arranged in series in the tube channel, and a manipulating wire engaged with the clips is arranged at the other tube channel.

17 Claims, 15 Drawing Sheets

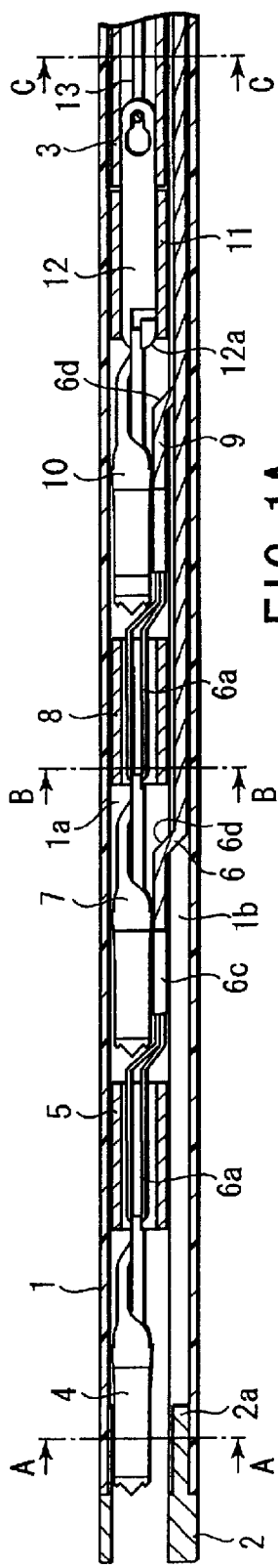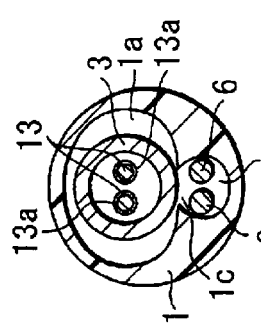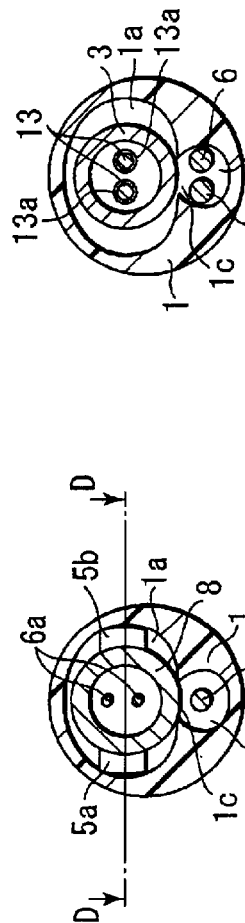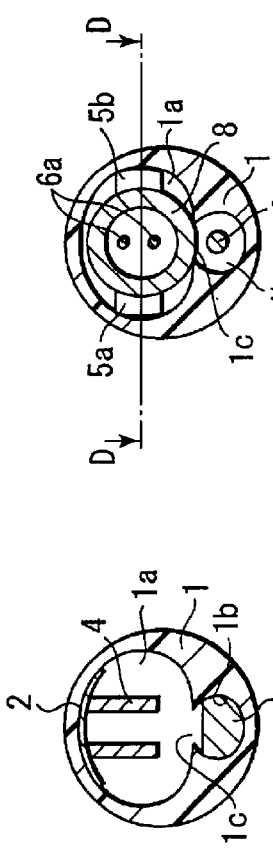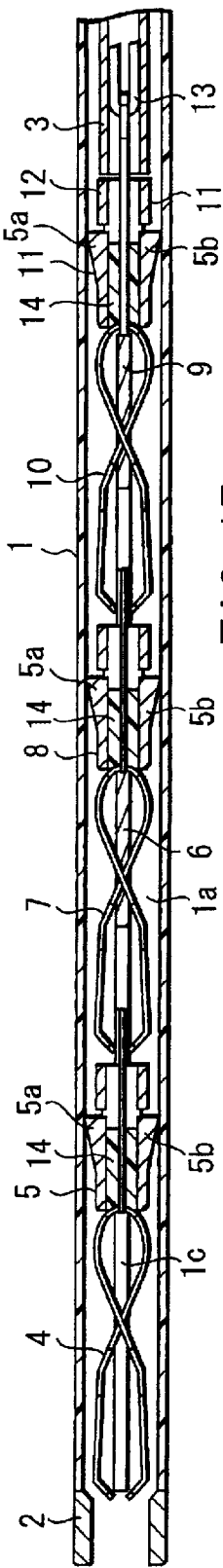

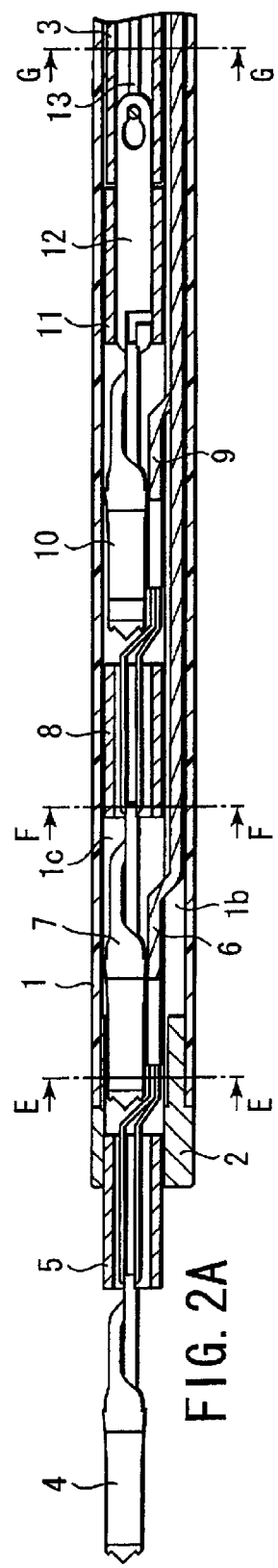
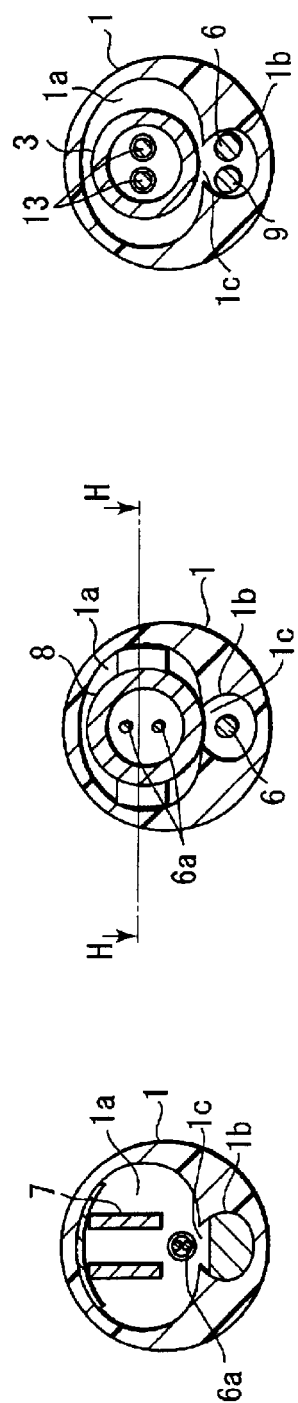
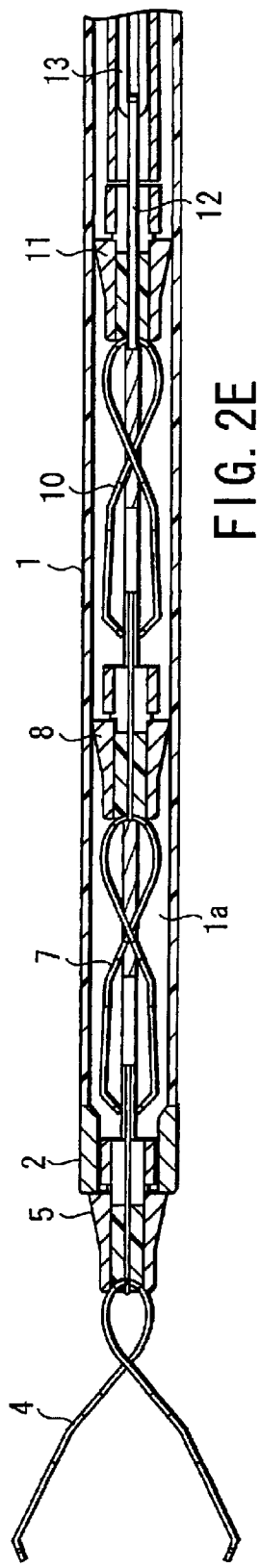
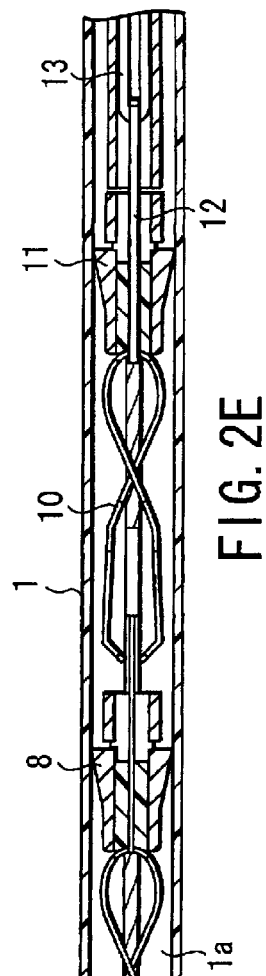
FIG. 2A  FIG. 2B  FIG. 2C  FIG. 2D  FIG. 2E

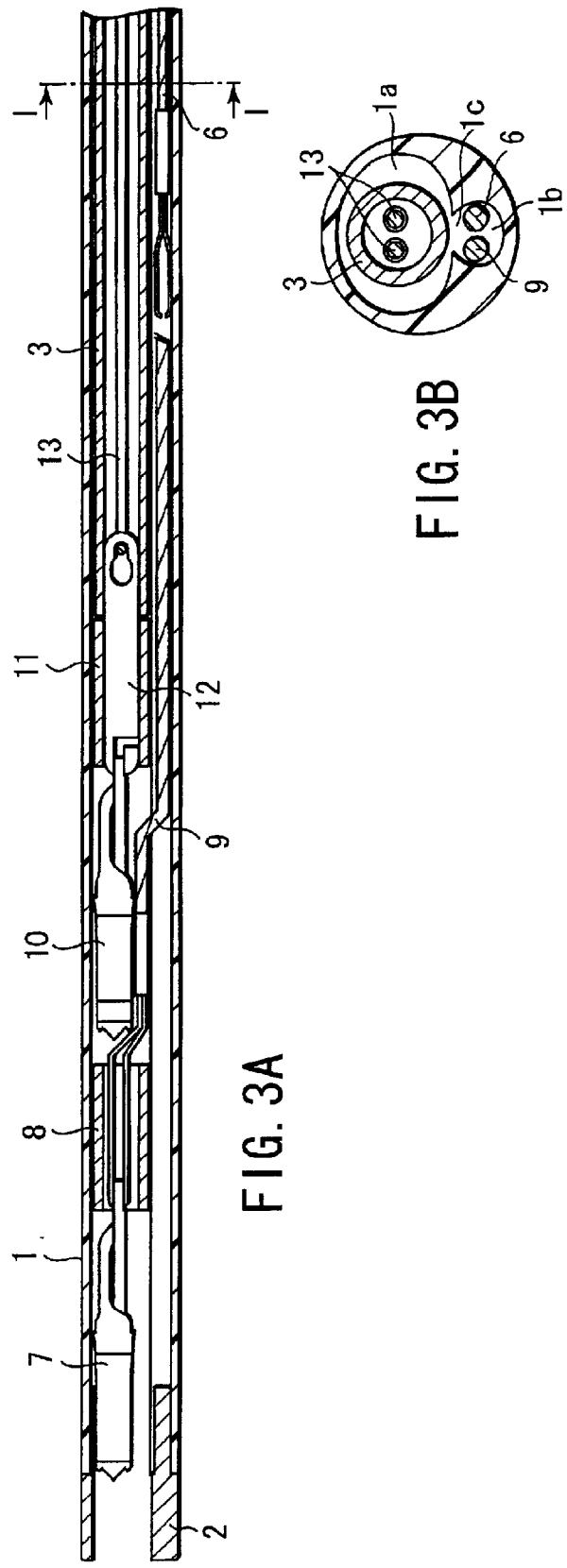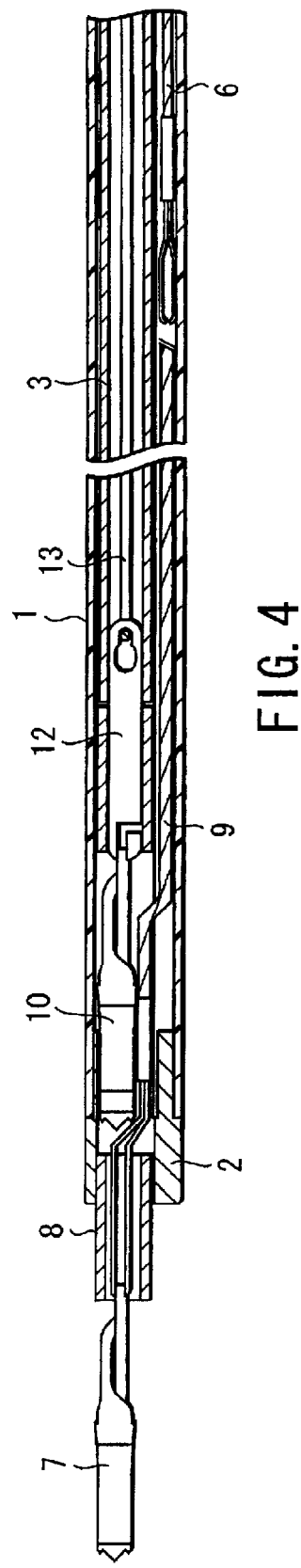

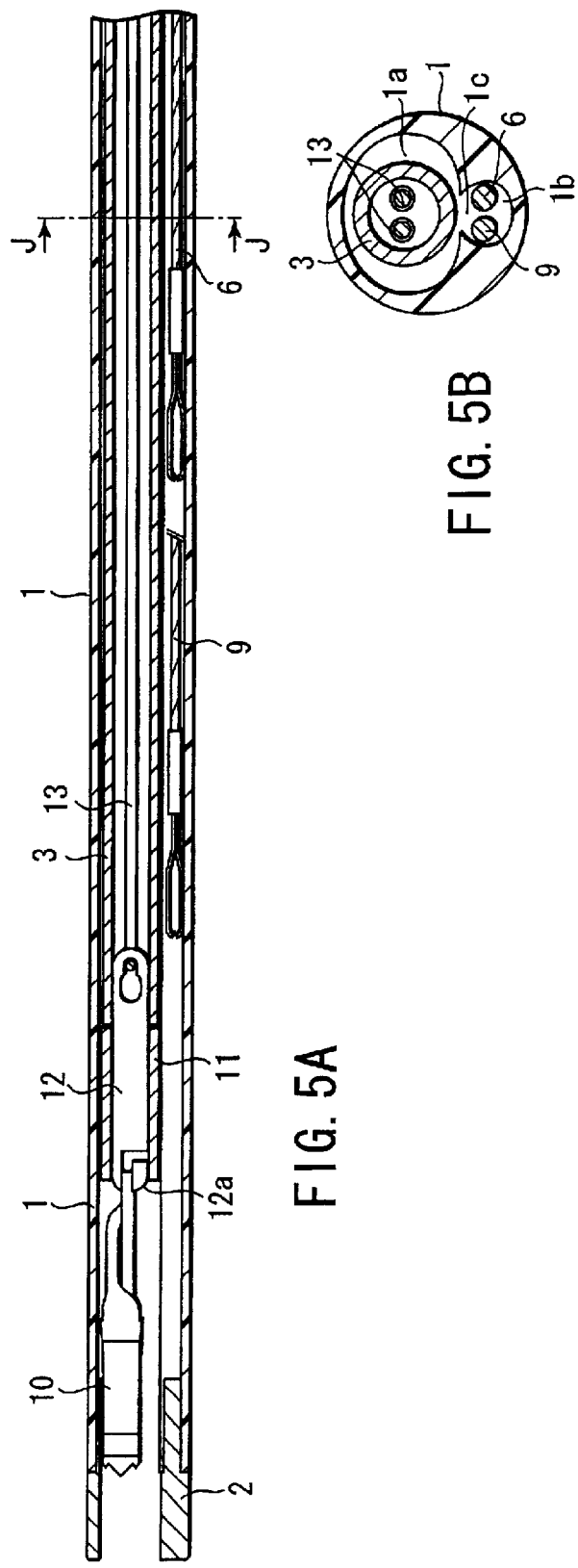
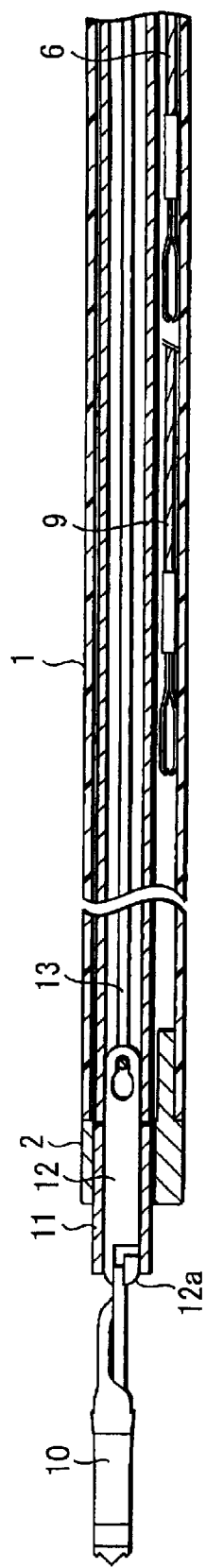

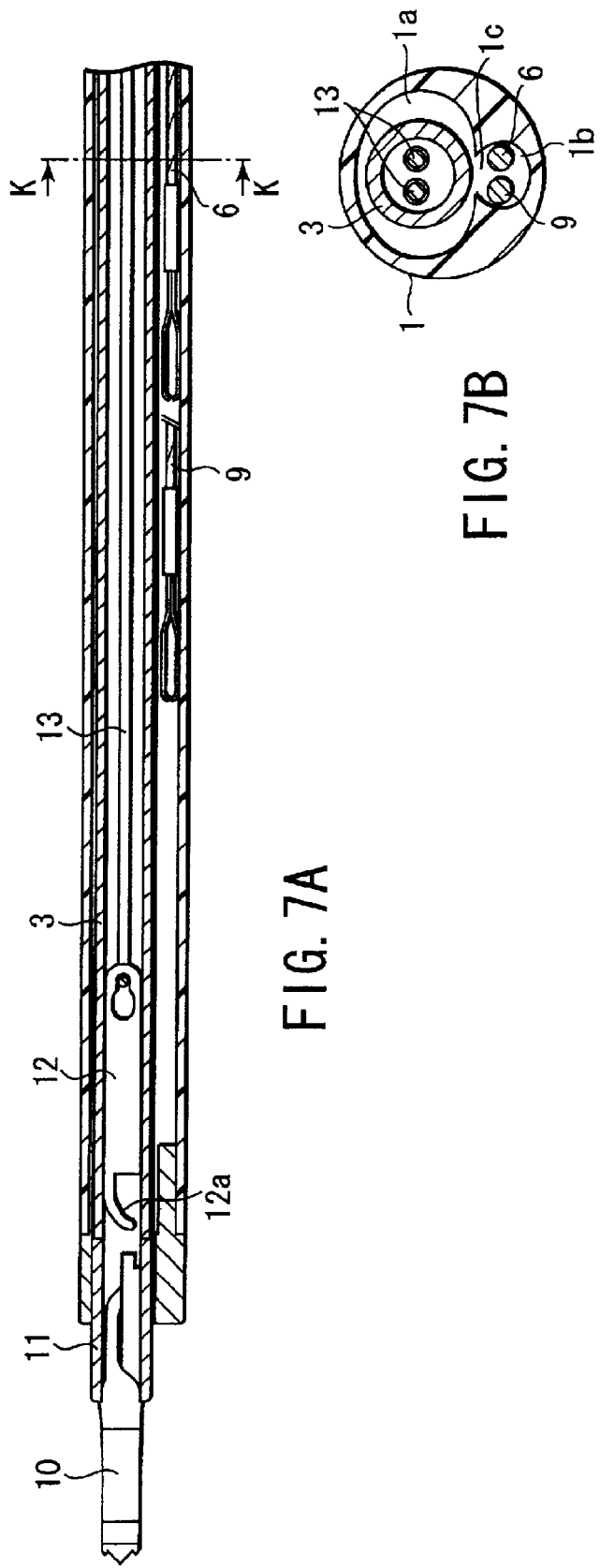

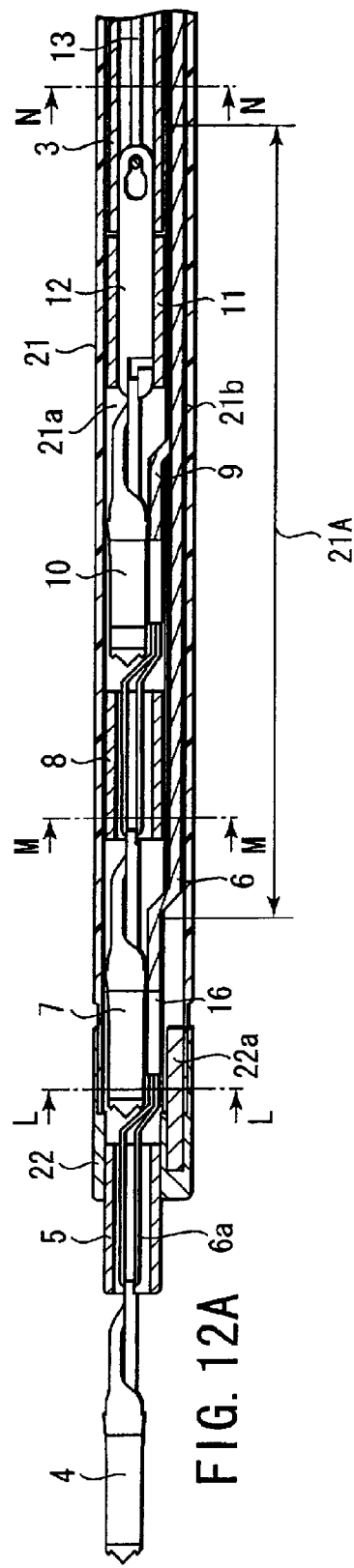
FIG. 12A
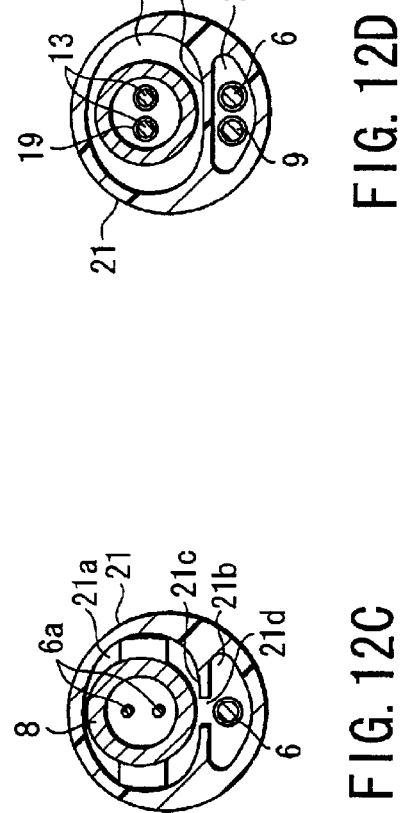
FIG. 12D
FIG. 12C
FIG. 12B

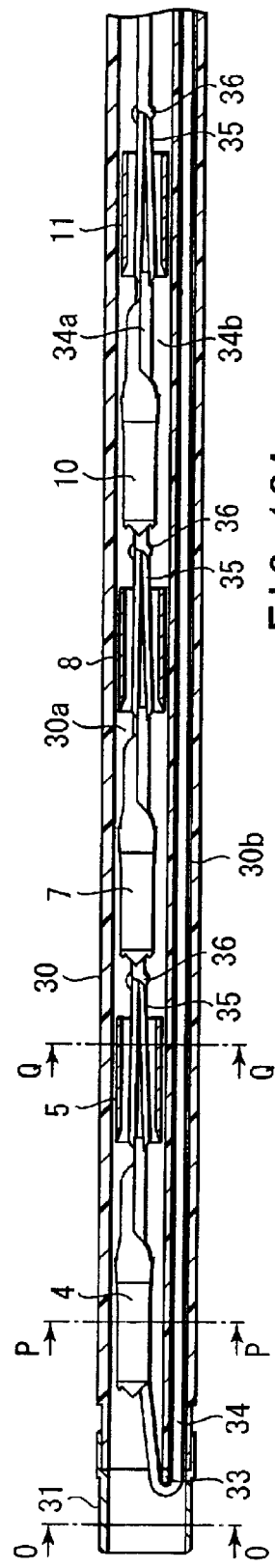
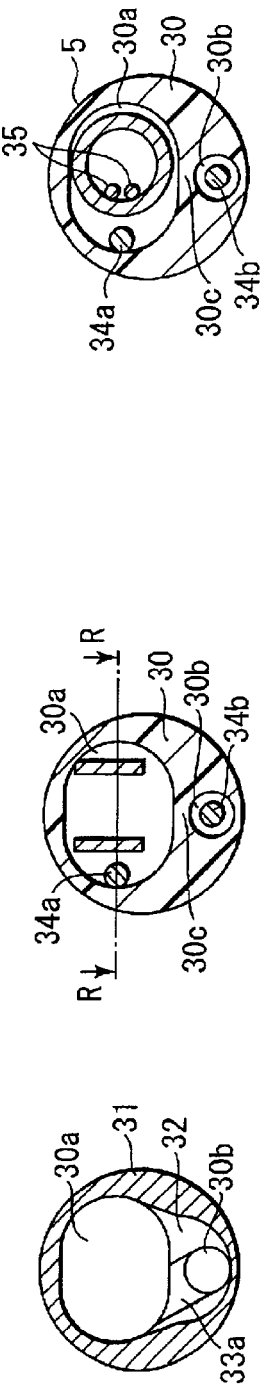
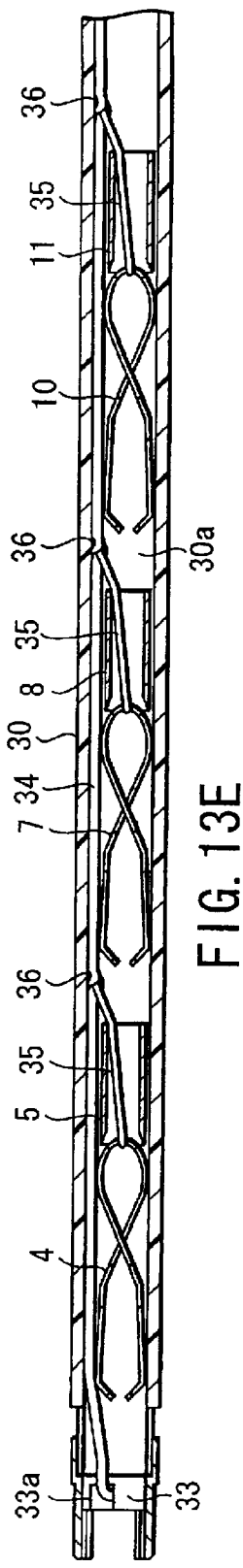
FIG. 13A
FIG. 13B
FIG. 13C
FIG. 13D
FIG. 13E

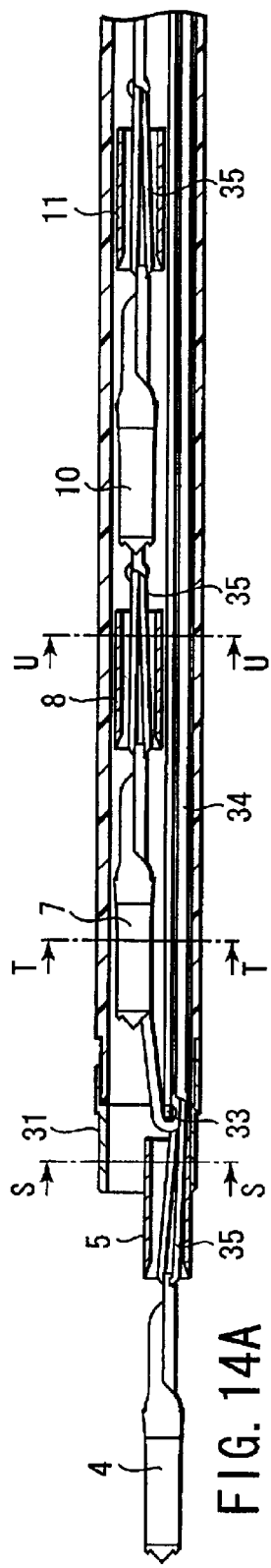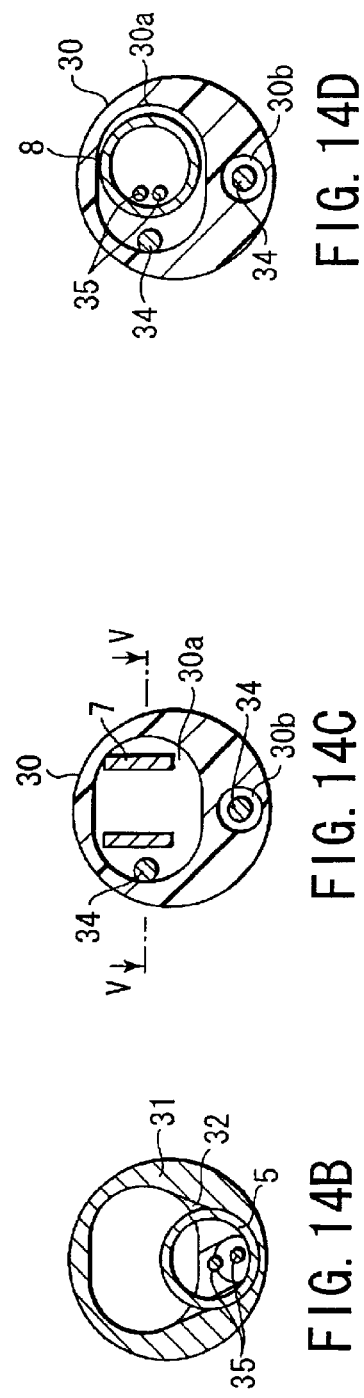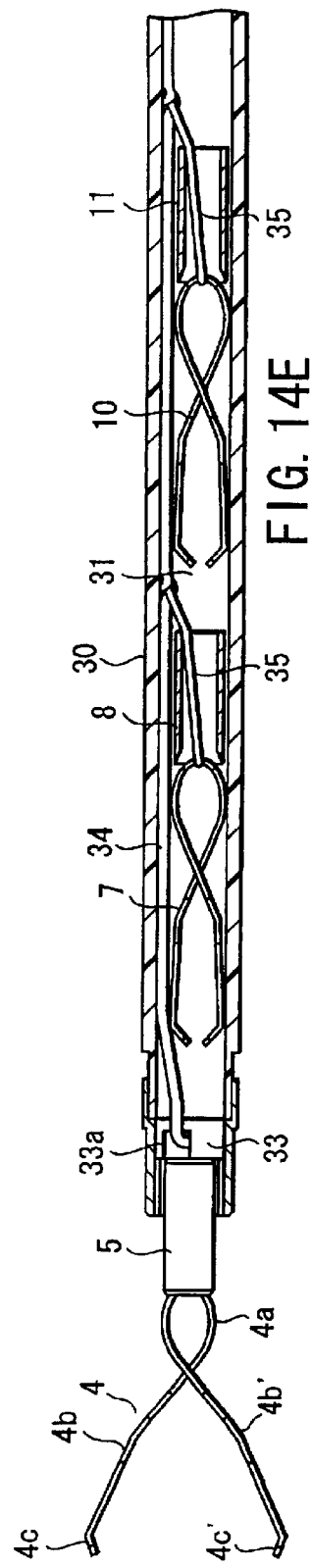

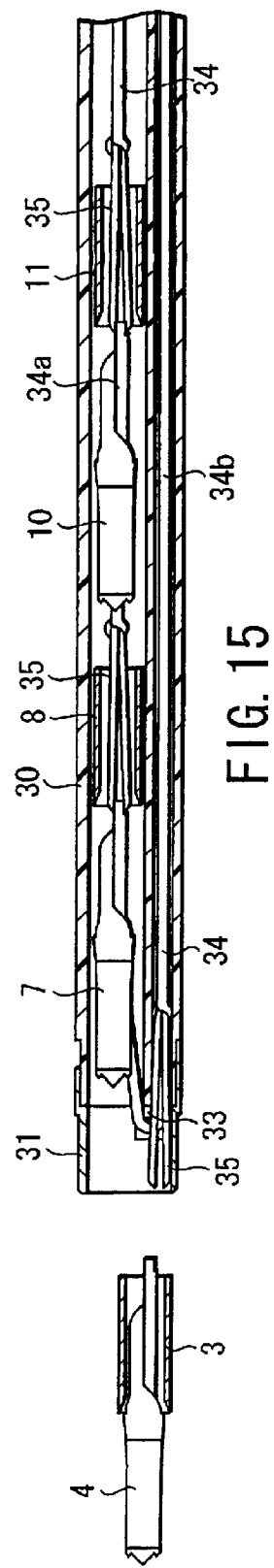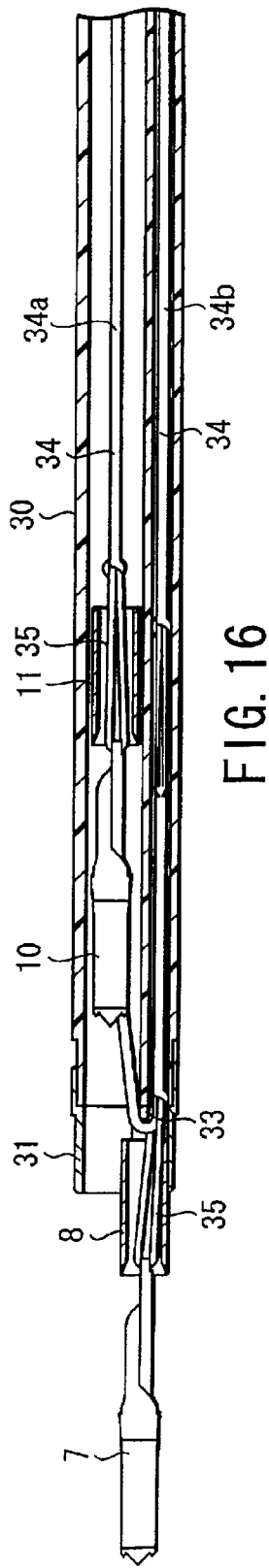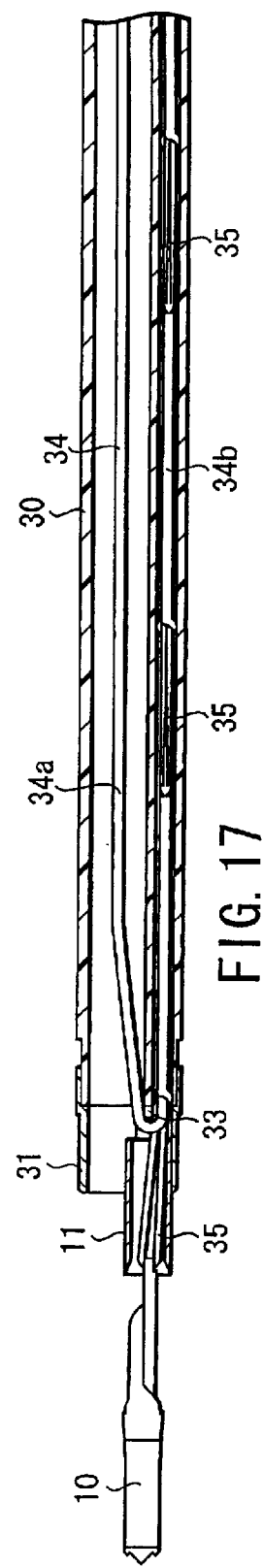

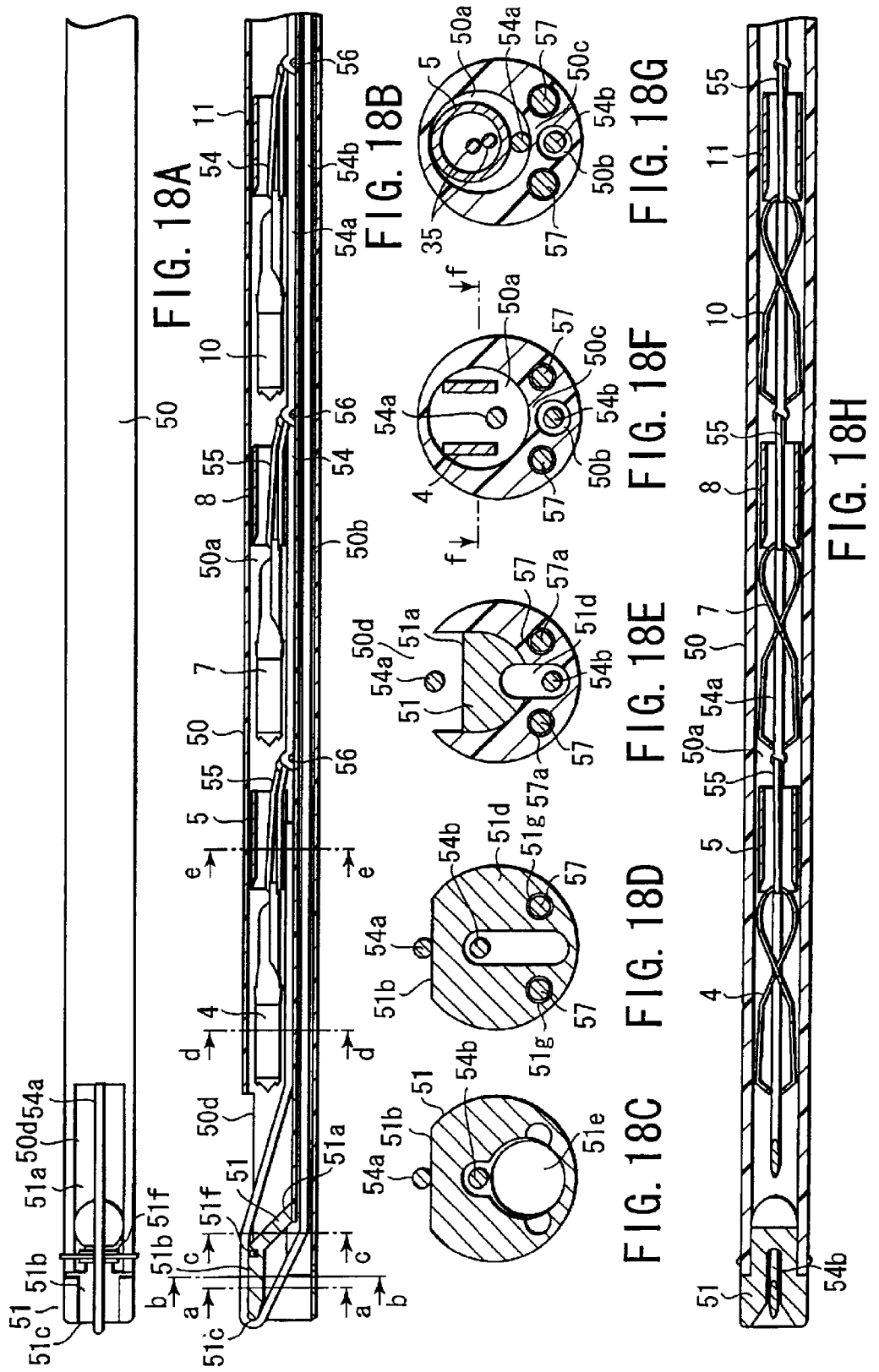

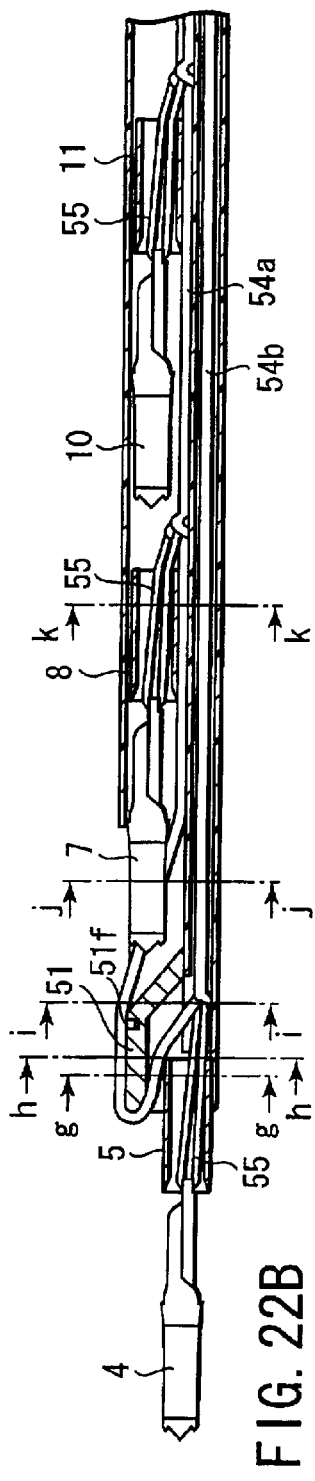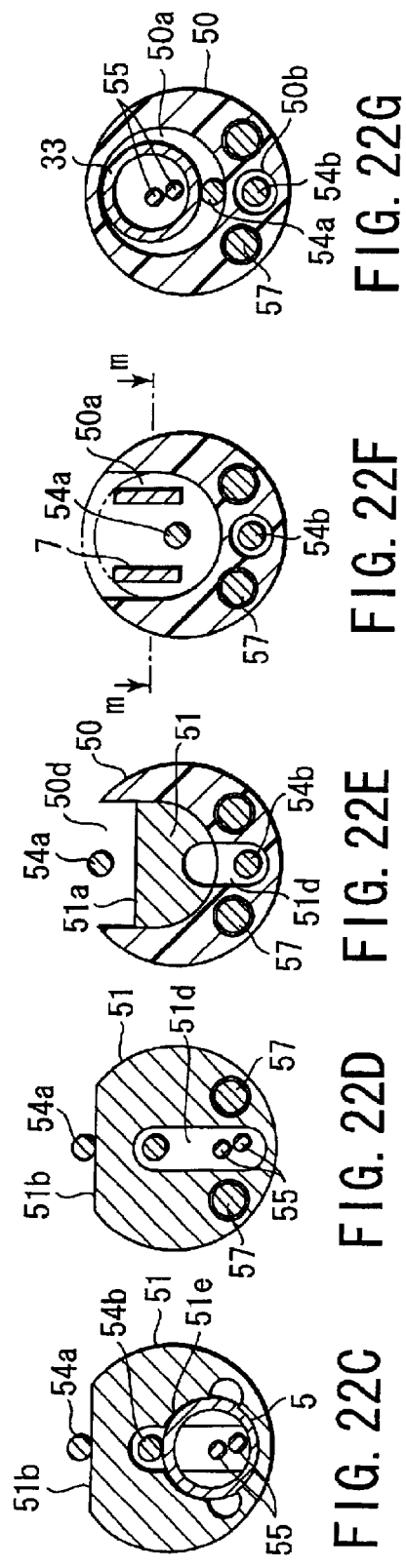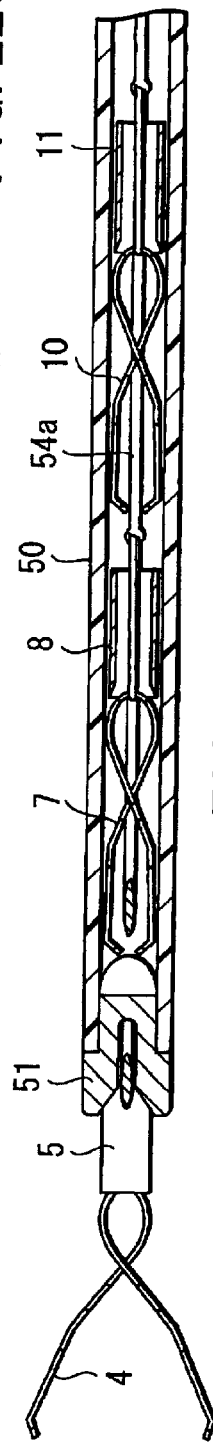

APPARATUS FOR LIGATING LIVING TISSUES

CROSS-REFERENCE TO RELATED APPLICATIONS

This application is based upon and claims the benefit of priority from the prior Japanese Patent Application No. 2001-088382, filed Mar. 26, 2001, the entire contents of which are incorporated herein by reference.

BACKGROUND OF THE INVENTION

1. Field of the Invention

The present invention relates to a living tissue ligating apparatus for ligating living tissues by inserting the apparatus into a living body cavity in a transendoscopic manner.

2. Description of the Related Art

Conventionally, it has been well known that apparatuses for clipping living tissues are disclosed in Jpn. UM. Appln. KOKAI Publication No. 2-6011 and Jpn. Pat. Appln. KOKAI Publication No. 63-267345. In Jpn. UM. Appln. KOKAI Publication No. 2-6011, a clip and a manipulating wire is engaged with each other via a hook provided at a distal end portion of the manipulating wire and a connecting member provided at a distal end of the hook, the connecting member having a hook.

In addition, in Jpn. Pat. Appln. KOKAI Publication No. 63-267345, a plurality of clips are incorporated in an introducing tube; the clips and manipulating member are connected with each other by a substance with its low melting point; and the substance with its low melting point is fused while it is inserted into a body cavity so as to continuously carry out a clip ligating work.

However, in the clipping apparatus disclosed in Jpn. UM. Appln. KOKAI Publication No. 2-6011, only one clip can be mounted on a distal end of the introducing tube. Thus, only one clip can be used each time it is inserted into a body cavity through a forceps channel of an endoscope. Thus, when a plurality of living tissues in the internal living body cavity are clipped, it has been necessary to do a work that the clipping apparatus is pulled out from the forceps channel of the endoscope every time, and the clips are mounted and inserted into the forceps channel again. Therefore, there has been a disadvantage that complicated and very time consuming work is required.

In addition, there are many disease cases requiring high emergency when a clip is applied to a bleeding site. In such disease cases, such a complicated and time consuming work has been very problematic.

In order to these problems in Jpn. Pat. Appln. KOKAI Publication No. 63-267345, there is disclosed a clipping apparatus capable of continuously carrying out ligation by inserting it into the forceps channel only one time. In the clipping apparatus disclosed, a plurality of clips are connected respectively with each other by a substance with its low melting point. Then, a temperature is controlled by a heating element provided at a tip end of a sheath of the clipping apparatus, whereby ligation is continuously carried out. That is, a structure is provided such that the heating element is heated up to a temperature at which the substance with its low temperature is fused, thereby disconnecting these clips from each other.

However, there has been a problem that providing the heating element at the distal end portion of the sheath complicates an equipment structure, and requires another heating source. In addition, in order to open a clip made of a shape memory material, it is required to heat the clip up to a predetermined transform temperature T1. That is, after the clip has been opened, it is possible to reliably control a relationship between a temperature T1 for opening the clip and a temperature T2 for fusing the substance with its low melting point in order to fuse the substance with its low melting point, and then, ligate living tissues. However, this temperature control has been very difficult. In the clipping apparatus disclosed in Jpn. Pat. Appln. KOKAI Publication No. 63-267345, heating means for generating a heat during clip opening and during clip ligation is required. Therefore, there has been a problem that a complicated and time consuming work is required during clipping ligation.

BRIEF SUMMARY OF THE INVENTION

The present invention has been made in view of the foregoing circumstance. It is an object of the present invention to provide a living tissue ligating apparatus in which a plurality of clips are arranged in an introducing tube, and the clips can be continuously ligated in living tissues while the introducing tube is inserted into the forceps channel one time.

According to the present invention, there is provided a living tissue ligating apparatus comprising:

an introducing tube capable of being inserted into a living body cavity;

a manipulating wire movably inserted into the introducing tube; and clips for ligating living tissues, the clips being arranged in the introducing tube, wherein the introducing tube has a plurality of tube channels, a plurality of clips are arranged in series at the one tube channel, and a manipulating wire engaged with the clips are arranged at the other tube channel.

With the above construction, a plurality of clips mounted in the introducing tube can be retained in a body cavity merely by inserting the clipping apparatus in the body cavity one time. This makes it unnecessary to do a work that the clipping apparatus is retracted to the outside of the body cavity every time one clip is retained in the body cavity, and clips are mounted again and inserted into the body cavity again. In this manner, a surgical operation time can be reduced, and thus, a patient's pain can be reduced. In addition, the manipulating wire is inserted into a tube channel other than that in which clips are arranged. Thus, the clips can be retained in the body cavity one by one speedily, easily, and reliably without interference between the clips each and manipulating wire.

According to the present invention, there is provided a living tissue ligating apparatus comprising:

an introducing tube capable of being inserted into a living body cavity;

a manipulating wire movably inserted into the introducing tube; and clips for ligating living tissues arranged in the introducing tube, wherein the manipulating wire forms a loop section in close proximity to a distal end of the introducing tube, at least one wire extending from the loop section is extended at a proximal end portion of the introducing tube, a plurality of clips are securely fixed to one wire while the loop section is sandwiched between these clips, and retracting means is securely fixed to the proximal end side of the other wire.

With the foregoing construction, even if there is no compression member for extruding clips, the clips can be protruded by retracting the returned manipulating wire.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiment of the invention, and together with the general description given above and the detailed description of the embodiment given below, serve to explain the principles of the invention.

FIG. 1A is a longitudinal side section showing a distal end portion in a living tissue ligating apparatus according to a first embodiment of the present invention;

FIG. 1B is a sectional view taken along the line A—A of FIG. 1A;

FIG. 1C is a sectional view taken along the line B—B of FIG. 1A;

FIG. 1D is a sectional view taken along the line C—C of FIG. 1A;

FIG. 1E is a sectional view taken along the line D—D of FIG. 1C;

FIG. 2A is a longitudinal side section showing a distal end portion in the ligating apparatus illustrating the working of the present embodiment;

FIG. 2B is a sectional view taken along the line E—E of FIG. 2A;

FIG. 2C is a sectional view taken along the line F—F of FIG. 2A;

FIG. 2D is a sectional view taken along the line G—G of FIG. 2A;

FIG. 2E is a sectional view taken along the line H—H of FIG. 2C;

FIG. 3A is a longitudinal side section showing a distal end portion in the ligating apparatus according to the working of the present embodiment;

FIG. 3B is a sectional view taken along the line I—I of FIG. 3A;

FIG. 4 is a longitudinal side section showing a distal end portion in the ligating apparatus according to working of the present embodiment;

FIG. 5A is a longitudinal side section showing a distal end portion in the ligating apparatus according to working of the present embodiment;

FIG. 5B is a sectional view taken along the line J—J of FIG. 5A;

FIG. 6 is a longitudinal side section showing a distal end portion in the ligating apparatus according to working of the present embodiment;

FIG. 7A is a longitudinal side section of a distal end portion in the ligating apparatus according to working of the present embodiment;

FIG. 7B is a sectional view taken along the line K—K of FIG. 7A;

FIG. 12A is a longitudinal side view showing a distal end portion in a living tissue ligating apparatus according to a second embodiment of the present invention;

FIG. 12B is a sectional view taken along the line L—L of FIG. 12A;

FIG. 12C is a sectional view taken along the line M—M of FIG. 12A;

FIG. 12D is a sectional view taken along the line N—N of FIG. 12A;

FIG. 13A is a longitudinal side section showing a distal end portion in a ligating apparatus according to working of a third embodiment of the present invention;

FIG. 13B is a sectional view taken along the line O—O of FIG. 13A;

FIG. 13C is a sectional view taken along the line P—P of FIG. 13A;

FIG. 13D is a sectional view taken along the line Q—Q of FIG. 13A;

FIG. 13E is a sectional view taken along the line R—R of FIG. 13C;

FIG. 14A is a longitudinal side section showing a distal end portion in the ligating apparatus according to working of the present embodiment;

FIG. 14B is a sectional view taken along the line S—S of FIG. 14A;

FIG. 14C is a sectional view taken along the line T—T of FIG. 14A;

FIG. 14D is a sectional view taken along the line U—U of FIG. 14A;

FIG. 14E is a sectional view taken along the line V—V of FIG. 14C;

FIG. 15 is a longitudinal side section showing a distal end portion in the ligating apparatus according to the present embodiment;

FIG. 16 is a longitudinal side section showing a distal end portion in the ligating apparatus according to the present embodiment;

FIG. 17 is a longitudinal side section showing a distal end portion in the ligating apparatus according to the present embodiment;

FIG. 18A is a plan view showing a distal end portion in a ligating apparatus according to a fourth embodiment of the present invention;

FIG. 18B is a sectional side section of the same;

FIG. 18C is a sectional view taken along the line "a—a" of FIG. 18B;

FIG. 18D is a sectional view taken along the line "b—b" of FIG. 18B;

FIG. 18E is a sectional view taken along the line "c—c" of FIG. 18B;

FIG. 18F is a sectional view taken along the line "d—d" of FIG. 18B;

FIG. 18G is a sectional view taken along the line "e—e" of FIG. 18B;

FIG. 18H is a sectional view taken along the line "f—f" of FIG. 18F;

FIG. 22B is a longitudinal side section of the same;

FIG. 22C is a sectional view taken along the line "g—g" of FIG. 22B;

FIG. 22D is a sectional view taken along the line "h—h" of FIG. 22B;

FIG. 22E is a sectional view taken along the line "i—i" of FIG. 22B;

FIG. 22F is a sectional view taken along the line "j—j" of FIG. 22B;

FIG. 22G is a sectional view taken along the line "k—k" of FIG. 22B;

FIG. 22H is a sectional view taken along the line "m—m" of FIG. 22F;

DETAILED DESCRIPTION OF THE INVENTION

Figure 8:
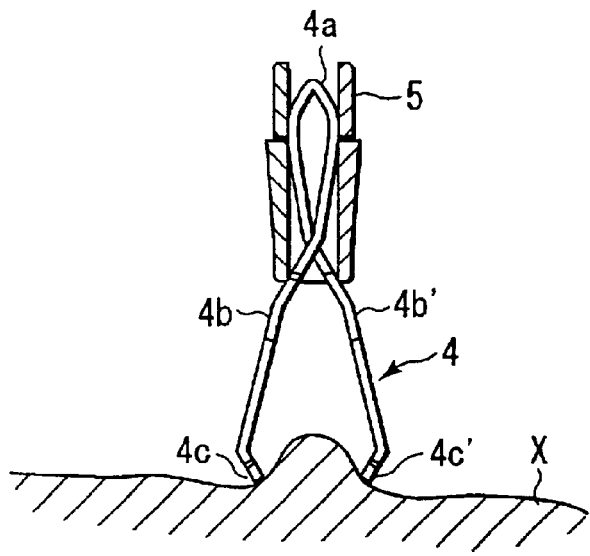
FIG. 8 is a longitudinal side section showing a state in which clips are retained in living tissues according to the working of the present invention.
Figure 9:
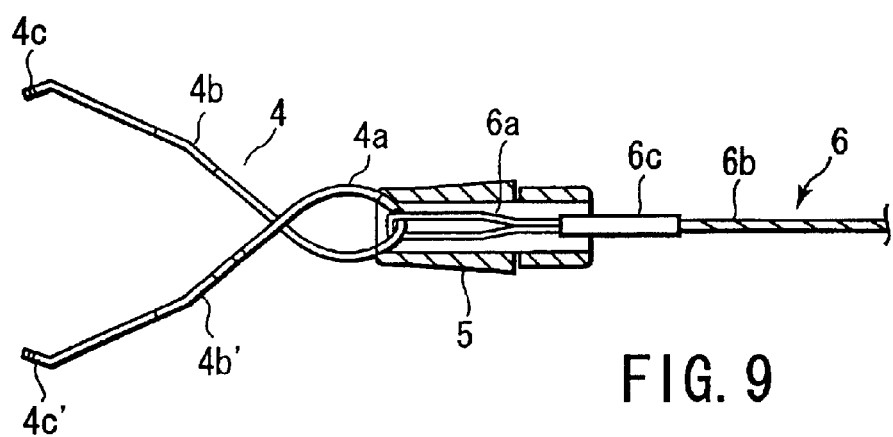
FIG. 9 is a longitudinal side section showing a state of connection between the clips each and the manipulating wire according to the present embodiment.

Hereinafter, preferred embodiments of the present invention will be described with reference to the accompanying drawings.

FIG. 1A to FIG. 11 show a first embodiment of the present invention. As shown in FIG. 1A and FIG. 1E, an introducing tube 1 has flexibility such that the tube can be inserted into an endoscope channel. A distal end tip 2 is provided at a distal end portion of this introducing tube 1. The introducing tube 1 is provided as a tune sheath that consists of a polymeric resin described later, for example, and a first tube channel 1a and a second tube channel 1b are provided in parallel to each other over an axial direction.

As shown in FIG. 1B to FIG. 1D, the first tube channel 1a is formed in a substantially oval shape on its transverse cross section, and has a large inner diameter so that a clip and a clip tightening ring described later can be inserted. The second tube channel 1b is also formed in a substantially oval shape on its transverse cross section, and has a small inner diameter so that a manipulating wire described later can be inserted. The first tube channel 1a and second tube channel 1b communicate with a communication channel 1c by being superimposed at a part of its sectional shape. Further, a distal end opening of the second tube channel 1b is closed by a proximal end portion 2a of the distal end tip 2.

This distal end tip 2 is fixed to the distal end portion of the introducing tube 1 by means of welding, adhesive, or press-fit. A compression member 3 is movably inserted into the first tube channel 1a of the introducing tube 1. A manipulating wire 13 is inserted into the compression member 3. Manipulating wires 6 and 9 are movably inserted into the second tube channel 1b. Clips 4 and 7 that are freely protruded and recessed from a distal end portion of the introducing tube 1 are removably connected to the distal end portion of the manipulating wires 6 and 9 each. In addition, the clip 10 that is freely protruded and recessed from the distal end portion of the introducing tube 1 is removably connected to the distal end portion of the manipulating wire 13 via a connecting plate 12.

The introducing tube 1 is provided as a tube sheath made of a polymeric resin (such as synthetic polymeric polyamide, high density/low density polyethylene, polyester, polytetrafluoro ethylene, tetrafluoro ethylene-perfluoroalkylivinyl ether copolymer, tetrafluoro ethylene-hexafluoro propylene copolymer). In this case, the internal and external faces of the sheath have slipping properties, thus making it easy to insert the tube into, and remove it from, an endoscope channel, protrude the clips 4, 7, and 10, and insert the manipulating wires 6, 9, and 13.

In addition, the introducing tube 1 is provided as a double tube having an inner layer and an outer layer at its external wall portion, and may be a tube sheath embedded while a reinforce member is interposed between the double tubes. In this case, the inner layer and outer layer are formed of the above polymeric resin. The reinforce member is formed of a cylindrically-shaped blade knitted with a thin metal line in a lattice shape, for example. In this manner, even when a force of compressing a sheath against the distal end portion and proximal end portion of the sheath, this sheath has its excellent compression resistance as compared with a tube sheath in which no reinforce member is embedded, and the sheath is free of being broken.

Dimensionally, the introducing tube 1 has its outer diameter that the tube can be inserted into the endoscope channel. The thickness of the sheath is determined depending on the rigidity of its element material. The polymeric resin based tube is about 0.3 mm to 0.8 mm in thickness. There is an advantage that the thickness of the sheath can be reduced, and the inner diameter of the sheath can be increased by embedding the reinforce material.

The distal end tip 2 is provided as a metallic short tube (such as a stainless tube), and a blade provided at the clip tightening ring described later is dimensionally set so that the blade can be engaged with the tip. In addition, the most distal end of the distal end tip 2 is 1.5 mm to 3.3 mm in outer diameter, and the distal end top 2 is about 1.0 mm to 2.2 mm in inner diameter.

The compression member 3 has flexibility such that the member can be inserted into the first tube channel 1a of the introducing tube 1. This compression member is disposed backwardly of the clip tightening ring 11 described later, the ring being mounted in the introducing tube 1, and is provided to protrude the clips 4, 7, and 10 from the introducing tube 1.

In addition, the compression member 3 may be a coil sheath with its irregular internal and external faces on which a metallic wire (such as stainless wire) with its round shaped sectional face is closely wound or a rectangular coil sheath with its flat internal and external faces obtained after the wire cross section is made rectangular by breaking a metallic wire (such as stainless wire) whose sectional face is rounded, for example. In this case, a coil sheath with its large inner diameter can be provided as compared with a round shaped coil even if an element wire diameter of the same diameter is employed. This makes it easier to protrude the clips 4, 7, and 10, and insert a manipulating wire 13.

This compression member 3 is moved to the distal end side relevant to the introducing tube 1, thereby making it possible to protrude the clips 4, 7, and 10 and the clip tightening rings 5, 8, and 11 from the introducing tube 1.

Further, the compression member 3 may be a tube sheath made of a polymeric resin (such as synthetic polymeric polyamide, high density/low density polyethylene, polyester, polytetrafluoro ethylene, tetrafluoro ethylene-perfluoroalkylivinyl ether copolymer, tetrafluoro ethylene-hexafluoro propylene copolymer). When this compression member is provided as a tube sheath, the sheath has slipping properties on its internal and external faces, thus making it easy to insert the introducing tube 1 in the first tube channel 1*a* and insert the manipulating wire 13.

In addition, the compression member 3 is provided as a double tube having an inner layer and an outer layer at its wall portion, and may be a tube sheath embedded while a reinforce member is interposed between the double tubes. In this case, the inner layer and outer layer are formed of the above polymeric resin. The reinforce member is formed of a cylindrically shaped blade knitted with a thin metal line in a lattice shape, for example. In this manner, even when a force of compressing a sheath against the distal end portion and proximal end portion of the sheath, this sheath has its excellent compression resistance as compared with a tube sheath in which no reinforce member is embedded, and the sheath is free of being broken.

Dimensionally, the compression member 3 has an outer diameter such that the member can be inserted into the first tube channel 1*a* of the introducing tube 1 and an inner diameter such that the manipulating wire 13 can be inserted. The outer diameter should be defined to be 3 mm or less in diameter, and the inter diameter should be as large as possible. However, the compression member requires thickness such that the protrusion force quantity can be reliably transmitted, and, even if a force is applied to be protruded to the clips 4, 7, and 10, no breakage occurs.

The clips 4, 7, and 10 are identical to each other in structure. A description of the clip 4 will be given here. As shown in FIG. 8, a metallic thin band plate is returned at its center portion, and its returned portion is defined as a proximal end portion 4*a*. Then, both arm sections 4*b* and 4*b'* extending from this proximal end portion 4*a* are returned in an expanding/opening direction. Further, the distal end rim portions of the arm sections 4*b* and 4*b'* each are returned so as to face to each other, and are defined as pinch sections 4*c* and 4*c'*. One of the distal ends of the pinch sections 4*c* and 4*c'* is formed to be protruded, and the other is formed to be recessed so as to easily pinch living tissues. Then, the opening/expanding properties are imparted to the arm sections 4*b* and 4*b'* so as to open the pinch section 4*c*.

A thin band plate of the clip 4 is made of stainless having resilience, whereby the clip is made rigid and is capable of reliably pinching living tissues. For example, by applying an ultra-elastic alloy such as nickel-titanium alloy, the expanding/opening properties are imparted to the arm sections 4*b* and 4*b'*, whereby the arm sections 4*b* and 4*b'* open more reliably than when they are protruded from the sheath.

In addition, the band plate of the clip 4 is 0.15 mm to 0.3 mm in thickness; the pinch sections 4*c* and 4*c'* are 0.5 mm to 1.2 mm in plate width; and the arm sections 4*b* and 4*b'* are 0.5 mm to 1.5 mm in plate width. The proximal end portion 4*a* is 0.3 mm to 0.5 mm in plate width.

Figure 10:
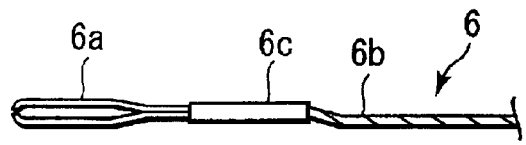
FIG. 10 is a side view showing a manipulating wire according to the present embodiment.

The manipulating wires 6 and 9 are identical to each other in structure. A description of the manipulating wire 6 will be given here. As shown in FIG. 10, the manipulating wire 6 is composed of a loop wire 6*a* and a proximal end wire 6*b*. The loop wire 6*a* is molded to be closed at a distal end of the proximal wire 6*b* composed of a metallic twisted wire. Only one twisted wire of the proximal wire 6*b* forms the loop wire 6*a*. When a core wire of the twisted wire is used for the loop wire 6*a*, good assembling properties are obtained. The core wire may be a twisted wire or a single wire. The loop wire 6*a* and proximal end wire 6*b* are bonded with each other via a metallic connecting pipe 6*c* by means of welding or adhesive.

The manipulating wires 6, 9 and 13 are, for example, stainless twisted wires. Such twisted wire is more flexible than the single wire, and flexibility of the introducing wire 1 itself is not degraded.

The manipulating wires 6, 9, and 13 may be coated with a polymeric resin 13*a* with its improved slipping properties such as high density/low density polyethylene or polytetrafluoro ethylene, for example. The optimal thickness of the coat is about 0.05 mm to 0.1 mm. Further, it is also efficient to apply emboss processing of 0.01 mm to 0.45 mm on the wire surfaces in order to improve the slipping properties of the manipulating wire 6, 9 and 13. Accordingly, the frictional resistance with an internal face of the introducing tube 1 decreases, and the traction force quantity can be transmitted up to a distal end of the introducing tube 1 without any loss. In this manner, ligating manipulation can be carried out with smaller force.

A force of 1 kg to 5 kg is applied to the loop wire 6*a* when the clip 4 is ligated. At this time, it is required to define dimensions such that the loop wire 4*a* breaks. The proximal end wire 4*b* is 0.3 mm to 0.8 mm in outer diameter, and the loop wire 4*a* is about 0.1 mm to 0.2 mm in diameter.

The thus-constructed manipulating wires 6 and 9 each have a bent portion 6*d* at which a wire at the proximal end side of the connecting pipe 6*c* is bent in a substantially crank shape. The manipulating wires 6 and 9 inserted into a second tube channel 1*b* advance into the first tube channel 1*a* when the bent portion 6*d* passes through a communicating channel 1*c*. The connecting pipe 6*c* and loop wire 6*a* are connected to the clips 4 and 7 in the first tube channel 1*a*.

In addition, the manipulating wire 13 is returned in close proximity to the distal end of the introducing tube. The distal end of the wire is connected to the proximal end portion of the connecting plate 12, and is inserted into the proximal end portion of the introducing tube. The distal end portion of this connecting plate 12 is connected to the proximal end portion 4*a* of the clip 10 via a claw 12*a* bent in a J shape.

Figure 11:
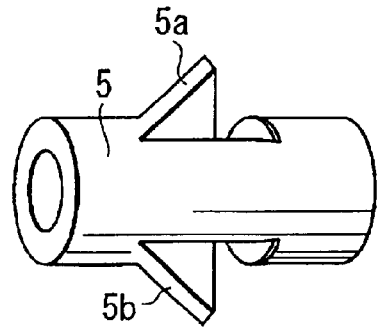
FIG. 11 is a perspective view showing a clip tightening ring according to the present embodiment.

The clip tightening rings 5, 8, and 11 are identical to each other in structure. A description of the clip tightening clip 5 will be given here. As shown in FIG. 11, the clip is molded of a resin or metal having rigidity and elasticity. Two blades 5*a* and 5*b* that are elastically deformed and freely protruded and recessed in a circumferential direction are provided at the outer periphery of the clip tightening ring 5. The number of blades 5*a* and 5*b* is not limited to two, and may be three or four. The blades 5*a* and 5*b* are inclined at their tip end side. These blades can be protruded from the introducing tube 1 and distal end tip 2 smoothly and without any resistance.

Further, the clip tightening ring 5 is mounted on the arms 4*b* and 4*b'* of the clip 4, thereby closing the arm sections 4*a* and 4*b'*. This ring is formed in a substantially tubular shape. The clip 4 and manipulating wire 6 are engaged with each other by hooking the loop wire 6*a* on the proximal end portion 4*a* of the clip 4. Even if the clip 4 is extruded by the manipulating wire 6, a polymeric material 14 such as silicone is engaged in the clip tightening ring, as shown in FIG. 1E, so that the engagement between the clip 4 and manipulating wire 6 can be maintained, and the clip 4 and clip tightening ring 5 can be temporarily fixed.

The blades 5a and 5b of the clip tightening ring 5 may be mounted in the first tube channel 1a of the introducing tube 1 in a folded state. However, the blades 5a and 5b are mounted on the introducing tube 1 in a protruded state, whereby the elasticity of the blades 5a and 5b can be maintained over a longer period of time. In addition, the contact resistance between an internal face of the introducing tube 1 and the blades 5a and 5b each decreases, thus making it possible to decrease the force quantity when the clip 4 is moved in the introducing tube 1.

The clip tightening ring 5 is injection-molded of a resin having rigidity and elasticity (such as polybutytelephthalate, polyamide, polyphenyl amide, liquid crystal polymer, polyether ketone, or polyphthalic amide). Alternatively, the ring is molded of an elastic metal (stainless or ultra-elastic alloy such as nickel titanium alloy), for example, by means of injection-molding, cutting processing, or plastic processing and the like.

A tubular portion of the clip tightening ring 5 is 0.6 mm to 1.3 mm in inner diameter and about 1.0 mm to 2.1 mm in outer diameter. The most outer diameter portion when the blades 5a and 5b are protruded is defined to be 1 mm or more considering the engagement with the distal end tip 2.

Now, working of a first embodiment will be described here.

The introducing tube 1 of the ligating apparatus is introduced into a body cavity via the channel of the endoscope inserted into the body cavity. Then, a distal end portion of the introducing tube 1 is located in close proximity to a clipping target tissue, for example, a gastric mucous membrane tissue. The compression member 3 is extruded in a distal end direction of the introducing tube 1, whereby a compression force is transmitted in order to the clip tightening ring 11, clip 10, clip tightening ring 8, clip 7, and clip tightening ring 5. Then, the most frontal clip 4 and clip tightening ring 5 are protruded from the distal end portion of the distal end tip 2.

The blades 5a and 5b of the clip tightening ring 5 are folded when they pass through the inside of the distal end tip 2. When they pass through the distal end tip 2, the blades 5a and 5b are protruded again. In this manner, the clip tightening ring 5 is prevented from entering the inside of the distal end tip 2 again.

While the pinch sections 4a and 4c' of the clip 4 are close to a target tissue, when the manipulating wire 6 is retracted, the blades 5a and 5b of the clip tightening ring 5 are engaged with an end face of the distal end tip 2. When the manipulating wire 6 is further retracted, an oval portion of the proximal end portion 4a of the clip 4 is retracted into the clip tightening ting 5. Dimensionally, the oval portion is greater than the inner diameter of the clip tightening ring 5, and the oval portion is crushed by the clip tightening ring S. Then, the arm sections 4b and 4b' expand and open significantly to the outside.

In this state, the clip 4 is guided so as to pinch a target living tissue. The manipulating wire 6 is further retracted, whereby the arm sections 4b and 4b' of the clip 4 are retracted into the clip tightening ring 5, and then, the pinch sections 4c and 4c' of the clip 4 are closed. While the living tissue is reliably pinched between the arm sections 4b and 4b' of the clip 4, when the manipulating wire 6 is further retracted, the loop wire 6a is broken, and the clip 4 and manipulating wire 6 are disengaged from each other. In this manner, as shown in FIG. 8, the clip 4 can be retained in a body cavity while a living tissue X is pinched.

Next, as shown in FIG. 3A, FIG. 3B, and FIG. 4, the manipulating wire 6 is retracted into the frontal side, and the compression member 3 is extruded in a distal end direction of the introducing tube 1 again. In this manner, a compression force is transmitted in order to the clip tightening ring 11, clip 10, and clip tightening ring 8, and a second clip 7 and a clip tightening ring 8 are protruded from the distal end portion of the distal end tip 2. In the same manner as that described previously, when the manipulating wire 9 is retracted while the pinch sections 4c and 4c' of the clip 7 are close to a target tissue, the blades 5a and 5b of the clip tightening ring 8 are engaged with an end face of the distal end tip 2. When the manipulating wire 9 is further retracted, the oval portion of the proximal end portion 4a of the clip 7 is retracted into the clip tightening ring 8. Then, the arm sections 4b and 4b' expand/open significantly to the outside.

In this state, the clip 7 is guided so as to pinch a target living tissue. The manipulating wire 9 is further retracted, whereby the arm sections 4b and 4b' of the clip 7 are retracted into the clip tightening ring 8, and the pinch sections 4c and 4c' of the clip 7 are closed. While a living tissue is reliably pinched between the arm sections 4b and 4b' of the clip 7, when the manipulating wire 9 is further retracted, the loop wire 6a is broken. Then, the clip 7 and manipulating wire 9 are disengaged from each other, and the clip 7 can be retained in a body cavity while the living tissue X is pinched.

Next, as shown in FIG. 5A, FIG. 5B, and FIG. 6, the manipulating wire 9 is introduced into the frontal side, and the compression member 3 is extruded in a distal end direction of the introducing tube 1 again. In this manner, a compression force is transmitted to a clip tightening ring 11, and a third clip 10 and the clip tightening ring 11 are protruded from the distal end portion of the distal end tip 2. Then, in the same manner as that described previously, while the pinch sections 4a and 4c' of the clip 10 are close to a target tissue, when a manipulating wire 13 is retracted, the blades 5a and 5b of the clip tightening ring 11 are engaged with an end face of the distal end tip 2. When the manipulating wire 13 is further retracted, the oval portion of the proximal end portion 4a of the clip 10 is retracted into the clip tightening ring 11. Then, the arm sections 4b and 4b' expand/open significantly to the outside.

In this state, the clip 10 is guided so as to pinch a target living tissue. The manipulating wire 13 is further retracted, whereby the arm sections 4b and 4b' of the clip 10 are retracted into the clip tightening ring 11, and the pinch sections 4c and 4c' of the clip 10 are closed. While the living tissue is reliably pinched between the arm sections 4b and 4b' of the clip 10, when the manipulating wire 13 is further retracted, a claw 12a bent in a J letter shape extends linearly; the proximal end portion 4a and connecting plate 12 of the clip 10 are separated from each other; the clip 10 and manipulating wire 13 are disengaged with each other; and the clip 10 can be retained in a body cavity while the living tissue X is pinched, as shown in FIG. 7A and FIG. 7B.

According to the first embodiment, a plurality of clips mounted in the introducing tube can be retained merely inserting the ligating apparatus in the body cavity one time. This makes it unnecessary to do a complicated work that the ligating apparatus is retracted to the outside of the body cavity every time one clip is retained in the body cavity, and the clip is mounted again and inserted into the body cavity again. In this manner, a surgical operation time can be reduced, and thus, a patient's pain can be reduced. In addition, the manipulating wire is inserted into a tube channel other than that in which clips are arranged. Thus, the clips can be retained speedily, easily, and reliably in the body cavity one by one without interference between the clips each and the manipulating wire.

FIG. 12A to FIG. 12D show a second embodiment of the present invention. Like constituent elements shown in the first embodiment are designated by like reference numerals. A duplicate description is omitted here.

An introducing tube 21 of the present embodiment is formed of a multi-lumen tube in which a first tube channel 21a and a second tube channel 21b are partitioned from each other by a bulkhead 21c. A communicating channel 21d consisting of a slit that communicates with the first tube channel 21a and the second tube channel 21b is provided at the bulkhead 21c in close proximity to a distal end portion of the introducing tube 21. Here, 21A indicates a slit length.

In addition, a pin 22a protruded at the proximal end side is provided at the distal end tip 22. This pin 22a is press-fitted to the second tube channel 21b to close a distal end opening of the second tube channel 21b. The other construction is the same as in the first embodiment, and working of the present embodiment is also the same as that of the first embodiment.

FIG. 13A to FIG. 17 show a third embodiment of the present invention. Like constituent elements shown in the first and second embodiments are designated by like reference numerals. A duplicate description is omitted here.

As shown in FIG. 13A to FIG. 13E, an introducing tube 30 has flexibility such that the tube can be inserted into the endoscope channel. A distal end tip 31 is provided at a distal end portion of this introducing tube 30. The introducing tube 30 is composed of a multi-lumen tube in which a first tube channel 30a whose transverse sectional face is formed in a substantially oval shape and a second tube channel 30b formed in a circular shape are partitioned from each other by a bulkhead 30c. A distal end tip 31 is provided at a distal end portion of the introducing tube 30.

The bulkhead 30c of the introducing tube 30 is cut out at the inside of the distal end tip 31, and the first tube channel 30a and the second tube channel 30b communicate with each other. At a distal end of the bulkhead 30c, an engaging stepped portion 32 engaged with the clip tightening rings 5, 8, and 11 is provided to be deflected to the second tube channel 30b side. In addition, a holding element 30 having a guide groove 33a for slidably guiding a manipulating wire described later is fixed to the distal end.

One manipulating wire 34 is movably inserted into the first tube channel 30a and the second tube channel 30b. This manipulating wire 34 is returned to form a loop section at the inside of the distal end tip 31, and the loop section is guided into a guide groove 33a of the holding element 33. Then, an advancing side 34a at one end side of the manipulating wire 34 is inserted into the first tube channel 30a, and a retracting side 34b at the other end is inserted into the second tube channel 30b.

It is desirable that this manipulating wire 34 has slipping properties and flexibility. For example, this wire is formed of a polymeric fiber such as polyparaphenylene benzobisoxazole, polyethylene, polyester, polypropylene, polyamide, or liquid crystal polymer.

At an intermediate portion of this manipulating wire 34, three loop shaped connecting wires 35 are securely fixed at the connecting portion 36 with predetermined intervals by means of fusion welding, adhesive, and another yarn binding. Then, the clips 4, 7, and 10 each similar to those according to the first embodiment are connected respectively to the connecting wire 35.

It is desirable that this connecting wire 35 have slipping properties and flexibility. For example, this wire is formed of a polymeric fiber such as polyparaphenylene benzobisoxazole, polyethylene, polyester, polypropylene, polyamide, or liquid crystal polymer. Then, the connecting wire can move freely on the manipulating wire 34 irrespective of advancement or retraction of the manipulating wire 34.

Now, working of a third embodiment will be described here.

The introducing tube 30 of the ligating apparatus is introduced into a body cavity via the endoscope channel inserted into the body cavity. Then, a distal end portion of the introducing tube 30 is located in close proximity of a clipping target tissue, for example, a gastric mucous membrane tissue. When a retracting side 34b of the manipulating wire 34 inserted into the second tube channel 30b is retracted to the frontal side of the introducing tube 30, the manipulating wire 34 is returned to form a loop section at a portion of the holding element 33. Then, an advancing side 34a of the manipulating wire 34 advances to the distal end side of the introducing tube 30. Therefore, as shown in FIG. 14A to FIG. 14E, the most frontal clip 4 and clip tightening ring 5 are protruded from the distal end portion of the distal end tip 31.

When the clip tightening ring 5 is located in the distal end tip 31, the ring drops in the engaging stepped portion 32. In this manner, the clip tightening ring 5 is prevented from entering the introducing tube 30 again.

While the pinch sections 4c and 4c' of the clip 4 are close to a target tissue, when the retracting side 34b of the manipulating wire 34 is retracted, a rear end of the clip tightening ring 5 is engaged with an engaging stepped portion 32. When the retracting side 34b of the manipulating wire 34 is retracted, the oval portion of the proximal end portion 4a of the clip 4 is retracted into the clip tightening ring 5. Dimensionally, the oval portion is greater than the internal diameter of the clip tightening ring 5. Thus, the oval portion is crushed by the clip tightening ring. Then, the arm sections 4b and 4b' expand/open significantly to the outside.

In this state, the clip 4 is guided so as to pinch a target living tissue. The retracting side 34b of the manipulating wire 34 is further retracted, whereby the arm sections 4b and 4b' of the clip 4 are retracted into the clip tightening ring 5, and the pinch sections 4c and 4c' of the clip 4 are closed. While a living tissue is reliably pinched between the arm sections 4b and 4b' of the clip 4, when the retracting side 34b of the manipulating wire 34 is further retracted, the connecting wire 35 is broken, and the clip 4 and manipulating wire 34 are disengaged from each other, as shown in FIG. 15. In this manner, the clip 4 can be retained in a body cavity while the living tissue is pinched.

Next, as shown in FIG. 16, the retracting side 34b of the manipulating wire 34 is retracted to the frontal side, and the second clip 7 and clip tightening ring 8 are protruded from the distal end tip 31. Then, in the same manner as that described previously, while the pinch sections 4c and 4c' of the clip 7 are close to the target tissue, when the retracting side 34b of the manipulating wire 34 is retracted, a rear end of the clip tightening ring 8 is engaged with the engaging stepped portion 32. When the retracting side 34b of the manipulating wire 34 is further retracted, the oval portion of the proximal end portion 4a of the clip 7 is retracted into the clip tightening ring 8. Then, the arm sections 4b and 4b' expand/open significantly to the outside.

In this state, the clip 7 is guided so as to pinch a target living tissue. The retracting side 34b of the manipulating wire 34 is further retracted, whereby the arm sections 4b and 4b' of the clip 7 are retracted into the clip tightening ring 8, and the pinch sections 4c and 4c' of the clip 7 are closed. While the living tissue is reliably pinched between the arm sections 4b and 4b' of the clip 7, when the retracting side 34b of the manipulating wire 34 is retracted, the connecting wire 35 is broken. Then, the clip 7 and wire 34 are disengaged from each other, and the clip 7 can be retained in a body cavity while the living tissue is pinched.

Next, as shown in FIG. 17, the retracting side 34b of the manipulating wire 34 is retracted to the frontal side, and the third clip 10 and clip tightening ring 11 are protruded from the distal end tip 31. Then, in the same manner as that described previously, while the pinch sections 4c and 4c' of the clip 10 are close to a target tissue, when the retracting side 34b of the manipulating wire 34 is retracted, a rear end of the clip tightening ring 11 is engaged with the engaging stepped portion 32. When the retracting side 34b of the manipulating wire 34 is further retracted, the oval portion of the proximal end portion 4a of the clip 10 is retracted into the clip tightening ring 11. Then, the arm sections 4b and 4b' expand and open significantly to the outside.

In this state, the clip 10 is guided so as to pinch a target living tissue. The retracting side 34b of the manipulating wire 34 is further retracted, whereby the arm sections 4b and 4b' of the clip 10 are retracted into the clip tightening ring 11, and the pinch sections 4c and 4c' of the clip 10 are closed. While the living tissue is reliably pinched between the arm sections 4b and 4b' of the clip 10, when the retracting side 34b of the manipulating wire 34 is retracted, the connecting wire 35 is broken. Then, the clip 7 and wire 34 are disengaged from each other, and the clip 7 can be retained in a body cavity while the living tissue is pinched.

According to the third embodiment, a plurality of clips mounted in the introducing tube can be retained in a body cavity merely by inserting the ligating apparatus into the body cavity one time. This makes it unnecessary to do a work that the clipping apparatus is retracted to the outside of the body cavity every time one clip is retained in the body cavity, and clips are mounted again and inserted into the body cavity again. Therefore, the clips can be retained in a body cavity one by one speedily, easily, and reliably. In this manner, a surgical operation time can be reduced, and thus, a patient's pain can be reduced. In addition, a compression member is eliminated, and one end of the manipulating wire is merely retracted, whereby the clips can be continuously protruded and ligated. In this manner, a construction and operation can be simplified. In addition, the introducing tube can be reduced in diameter.

FIG. 18A to FIG. 25 each show a fourth embodiment of the present invention. Like constituent elements shown in the first and third embodiments are designated by like reference numerals. A duplicate description is omitted here.

As shown in FIG. 18A to FIG. 18H, an introducing tube 50 has flexibility such that the tube can be inserted into the endoscope channel. A holding element 51 is provided at a distal end portion of this introducing tube 50. The introducing tube 50 is composed of a multi-lumen tube in which a first tube channel 50a whose transverse cross section is shaped in a large diameter circle and a second tube channel 50b shaped in a small diameter circle are partitioned by a bulkhead 50c. On the top face at the distal end portion of the introducing tube 50, a rectangular opening portion 50d is provided along an axial direction of the introducing tube 50. This opening portion communicates with the first tube channel 50a.

On the top face of the holding element 51 provided at the distal end portion of the introducing tube 50, an inclined face 51a with its upward gradient toward the distal end of the introducing tube 50 is provided in opposite to the opening portion 50d. A flat face 51b is continuously provided from the top portion of this inclined face 51a. A groove is provided partly of this flat face 51b. At the inside of this groove, a fiber yarn 51f is embedded in order to reliably fix the holding element 51 to the distal end of the introducing tube 50. This fiber yarn 51f is fixed to be reliably wound along the peripheral direction. Adhesive is applied to a portion around which the fiber yarn 51f is wound, whereby the fiber yarn can be fixed more reliably. At the distal end portion of the holding element 51, an arc shaped portion 51c is provided continuously from the flat face 51b.

In addition, a longitudinally-elongated wire channel 51d that communicates with the second tube channel 50b and inserts the manipulating wire 54 is provided at the low portion of the holding element 51. An circularly-opening engaging stepped portion 51e engaged with the clip tightening rings 5, 8, and 11 is provided at the front portion of this wire channel 51d.

One manipulating wire 54 is movably inserted into the first tube channel 50a and the second tube channel 50b. This manipulating wire 54 is returned to form a loop section at the arc shaped portion 51c of the holding element 51, and the loop section is guided to the wire channel 51d of the holding element 51. Then, an advancing side 54a at one end side of the manipulating wire 54 is inserted into the first tube channel 50a, and a retracting side 54b at the other end side is inserted into the second tube channel 50b.

It is desirable that this manipulating wire 54 has slipping properties and flexibility. The wire is formed of a polymeric fiber such as polyparaphenylene benzobisoxazole, polyethylene, polyester, polypropylene, polyamide, or liquid crystal polymer, for example.

At an intermediate portion of this manipulating wire 54, three loop shaped connecting wires 55 are securely fixed at the connecting portion 56 with predetermined intervals by means of fusion welding, adhesive, and another yarn binding. Then, the clips 4, 7, and 10 each similar to those according to the first and third embodiments are connected respectively to the connecting wire 55.

It is desirable that this connecting wire 55 has slipping properties and flexibility. For example, this wire is formed of a polymeric fiber such as polyparaphenylene benzobisoxazole, polyethylene, polyester, polypropylene, polyamide, or liquid crystal polymer. Then, the connecting wire can move freely on the manipulating wire 54 irrespective of advancement or retraction of the manipulating wire 54. A reinforce wire 57 is provided as a reinforce wire such as steel wire inserted into a lumen 57a in order to improve rigidity of the introducing tube 50 and strength of connection between the introducing tube 50 and holding element 51. This wire is disposed in pair while the second tube channel 5b is sandwiched.

Now, working of a fourth embodiment will be described here.

Figure 19:
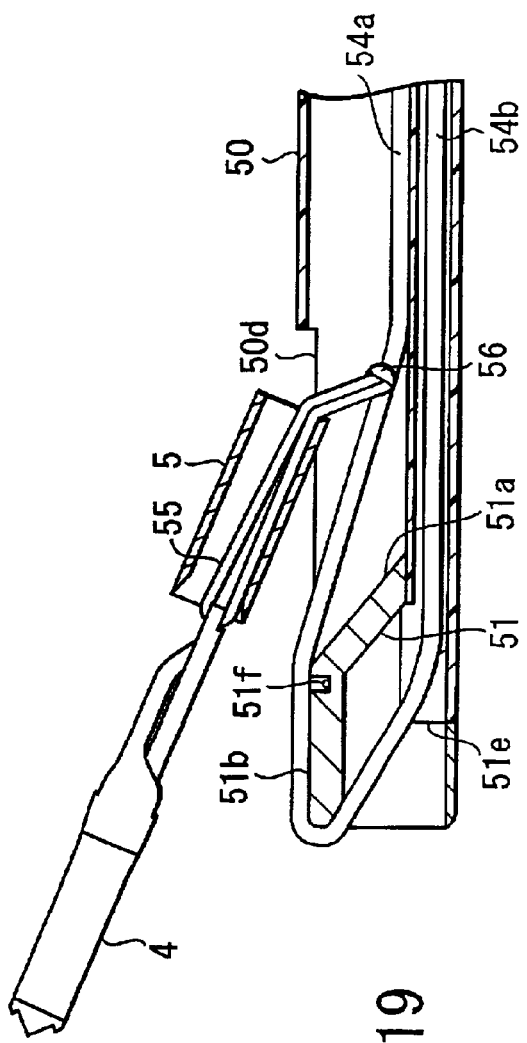
FIG. 19 is a longitudinal side section showing a distal end portion in the ligating apparatus according to working of the present invention.

The introducing tube 50 of the ligating apparatus is introduced into a body cavity via the channel of the endoscope inserted into the body cavity. Then, a distal end portion of the introducing tube 50 is located in close proximity to a clipping target tissue, for example, a gastric mucous membrane tissue. When the retracting side 54b of the manipulating wire 54 inserted into the second tube channel 50b is retracted to the frontal side, the manipulating wire 54 is returned to from a loop section at the arc shaped portion 51c of the holding element 51. Then, the advancing side 54a of the manipulating wire 54 advances to the distal end side of the introducing tube 50. Therefore, as shown in FIG. 19, the clip 4 and clip tightening ring 5 at the most frontal portion of the introducing tube 50 are protruded diagonally upwardly from the opening portion 50d.

Figure 20:
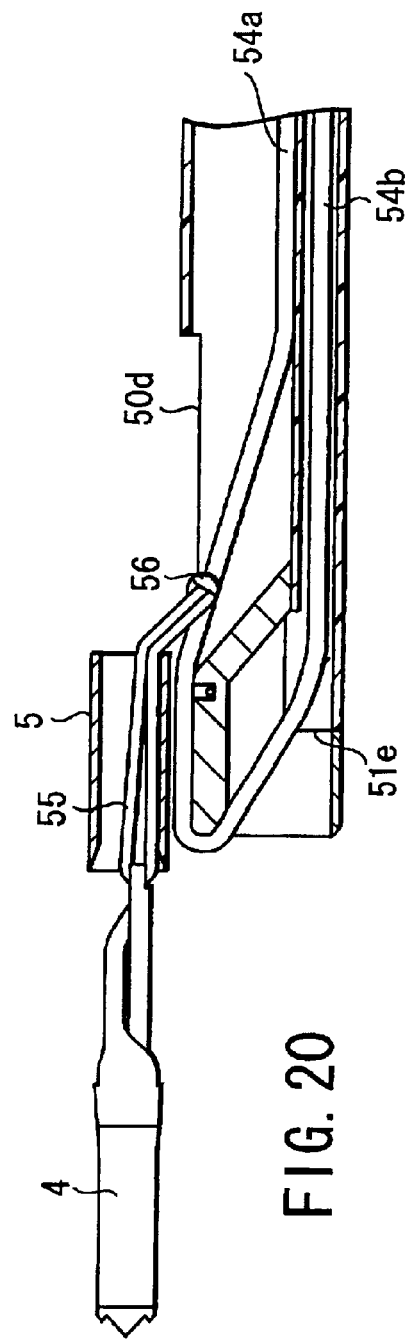
FIG. 20 is a longitudinal side section showing a distal end portion in the ligating apparatus according to working of the present invention.
Figure 21:
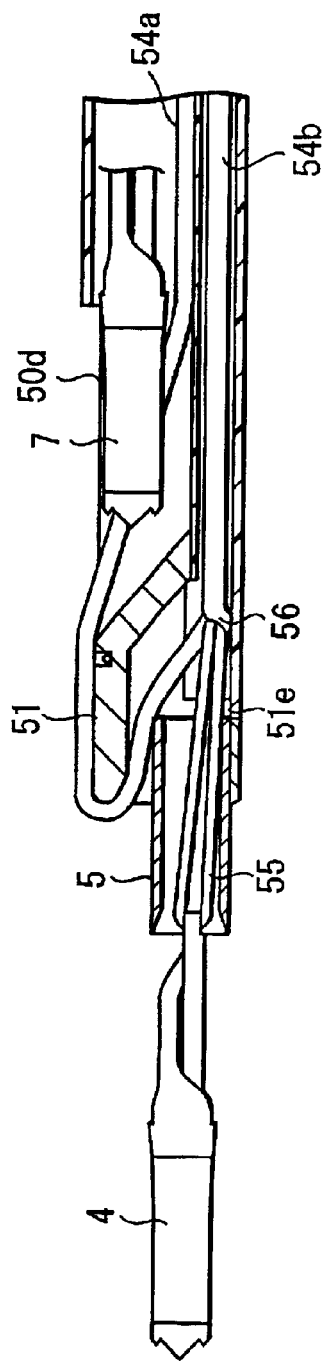
FIG. 21 a longitudinal side section showing a distal end portion in the ligating apparatus according to working of the present invention.

As shown in FIG. 20, when the clip tightening ring 5 is located on the top face of the flat face 51b of the holding element 51, the clip 4 and clip tightening ring 5 are substantially parallel to the introducing tube 50. When the retracting side 54b of the manipulating wire 54 is further retracted, the connecting portion 56 passes through the arc shaped portion 51c. As shown in FIG. 21, the clip tightening ring 5 drops in an engaging stepped portion 51e. In this manner, the clip tightening ring 5 is prevented from entering the introducing tube 50 again.

Figure 22A:
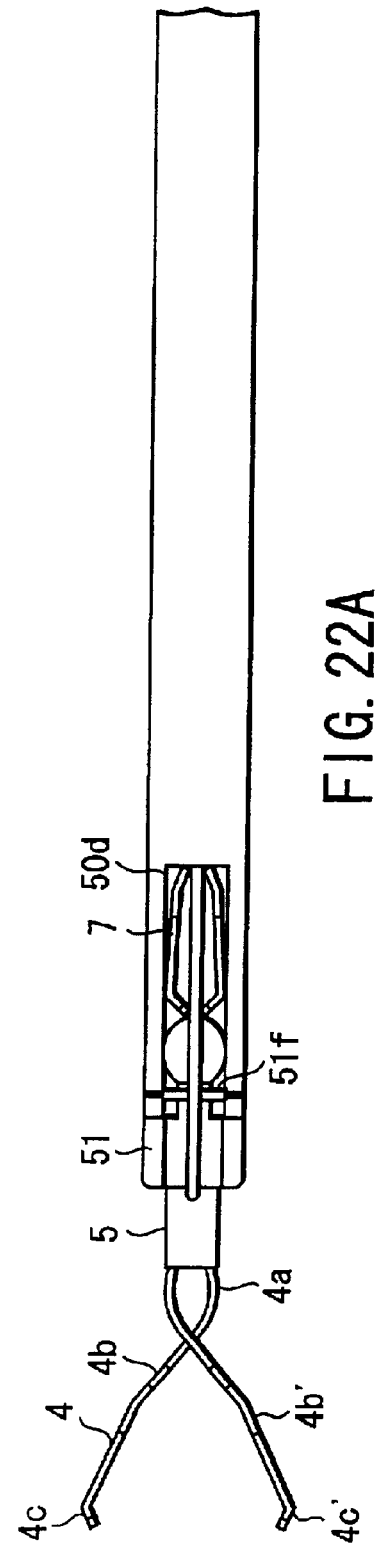
FIG. 22A is a plan view showing a distal end portion in the ligating apparatus according to working of the present invention.

While the pinch sections 4c and 4c' of the clip 4 are close to a target tissue, when the retracting side 54b of the manipulating wire 54 is retracted, a rear end of the clip tightening ring 5 is engaged with the engaging stepped portion 51e. When the retracting side 54b of the manipulating wire 54 is further retracted, the oval portion of the proximal end portion 4a of the clip 4 is retracted into the clip tightening ring 5. Dimensionally, the oval portion is greater than the inner diameter of the clip tightening ring 5, and thus, the oval portion is crushed by the clip tightening ring 5. Then, as shown in FIG. 22A and FIG. 22H, the arm sections 4b and 4b' expand/open significantly to the outside.

Figure 23:
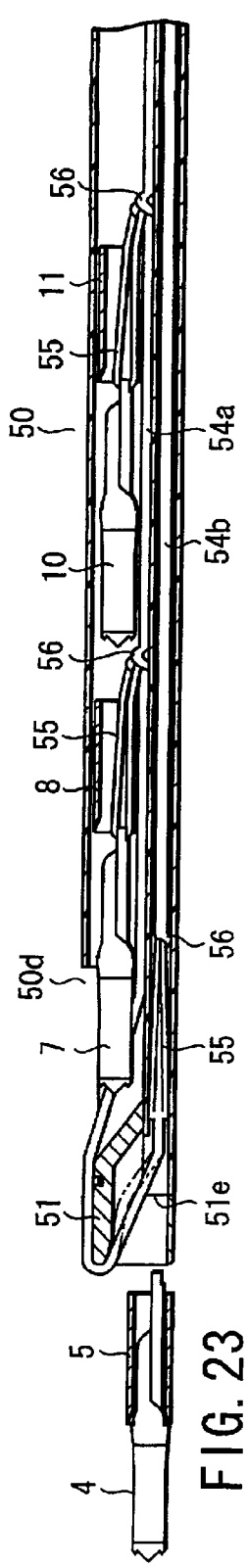
FIG. 23 is a longitudinal side section showing a distal end portion in the ligating apparatus according to working of the present invention.

In this state, the clip 4 is guided so as to pinch a target living tissue. The retracting side 54b of the manipulating wire 54 is further retracted, whereby the arm sections 4b and 4b' of the clip 4 are retracted into the clip tightening ring 5, and then, the pinch sections 4c and 4c' of the clip 4 are closed. While the living tissue is reliably pinched between the arm sections 4b and 4b' of the clip 4, when the retracting side 54b of the manipulating wire 54 is further retracted, the connecting wire 55 is broken, and the clip 4 and manipulating wire 54 are disengaged from each other, as shown in FIG. 23. In this manner, the clip 4 can be retained in a body cavity while a living tissue is pinched.

Next, the retracting side 54b of the manipulating wire 54 is retracted to the frontal side, the second clip 7 and clip tightening ring 8 are protruded from a distal end of the introducing tube 50. Then, in the same manner as that described previously, while the pinch sections 4c and 4c' of the clip 7 are close to a target tissue, when the retracting side 54b of the manipulating wire 54 is retracted, a rear end of the clip tightening ring 8 is engaged with the engaging stepped portion 51e. When the retracting side 54b of the manipulating wire 54 is further retracted, the oval portion of the proximal end portion 4a of the clip 7 is retracted into the clip tightening ring 8, and the arm sections 4b and 4b' expand/open significantly to the outside.

Figure 24:
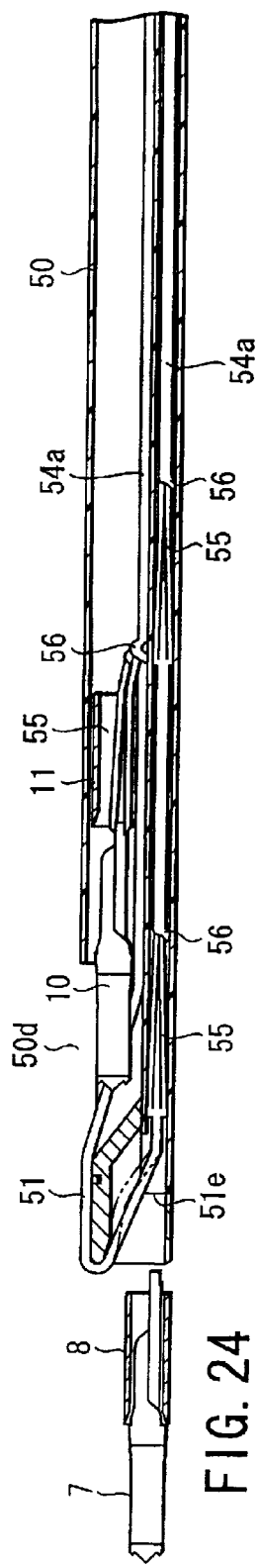
FIG. 24 is a longitudinal side section showing a distal end portion in the ligating apparatus according to working of the present invention.

In this state, the clip 7 is guided so as to pinch a target living tissue. The retracting side 54b of the manipulating wire 54 is further retracted, whereby the arm sections 4b and 4b' of the clip 7 are retracted into the clip tightening ring 8, the pinch sections 4c and 4c' of the clip 7 are closed. While the living tissue is reliably pinched between the arm sections 4b and 4b' of the clip 7, when the retracting side 54b of the manipulating wire 54 is further retracted, the connecting wire 55 is broken. Then, as shown in FIG. 24, the clip 7 and manipulating wire 54 are disengaged from each other, and the clip 7 can be retained in a body cavity while the living tissue is pinched.

Next, the retracting side 54b of the manipulating wire 54 is retracted to the frontal side, the third clip 10 and the clip tightening ring 11 are protruded from the distal end of the introducing tube 50. Then, in the same manner as that described previously, while the pinch sections 4c and 4c' of the clip 10 are close to a target tissue, when the retracting side 54b of the manipulating wire 54 is retracted, a rear end of the clip tightening ring 11 is engaged with an engaging stepped portion 51e. When the retracting side 54b of the manipulating wire 54 is further retracted, the oval portion of the proximal end portion 4a of the clip 10 is retracted into the clip tightening ring 11. Then, the arm sections 4b and 4b' expand/open significantly to the outside.

Figure 25:
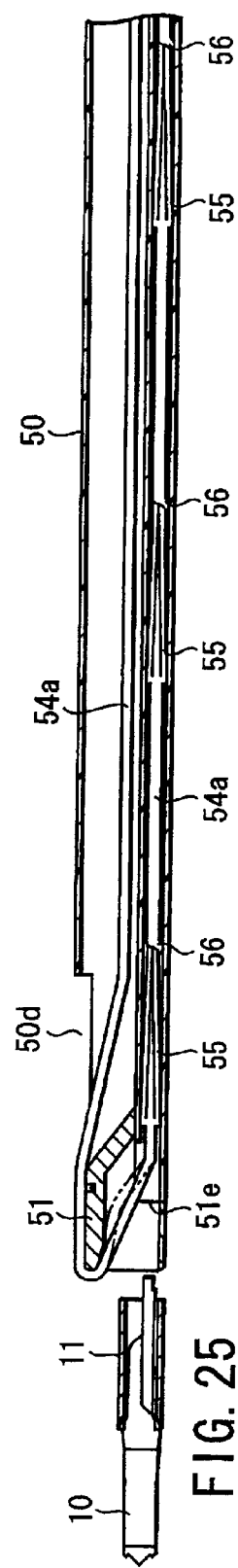
FIG. 25 is a longitudinal side section showing a distal end portion in the ligating apparatus according to working of the present invention.

In this state, the clip 10 is guided so as to pinch a target living tissue. The retracting side 54b of the manipulating wire 54 is further retracted, whereby the arm sections 4b and 4b' of the clip 10 are retracted into the clip tightening ring 11, and the pinch sections 4c and 4c' of the clip 10 are closed. While the living tissue is reliably pinched between the arm sections 4b and 4b' of the clip 10, when the retracting side 54b of the manipulating wire 54 is further retracted, the connecting wire 55 is broken. Then, as shown in FIG. 25, the clip 7 and manipulating wire 54 are disengaged from each other, and the clip 7 can be retained in a body cavity while the living tissue is pinched.

According to the fourth embodiment, a plurality of clips mounted in an introducing tube can be retained in a body cavity merely by inserting the ligating apparatus one time. This makes it unnecessary to do a work that the clipping apparatus is retracted to the outside of the body cavity every time one clip is retained in the body cavity, and clips are mounted again and inserted into the body cavity again. Therefore, the clips can be retained in a body cavity one by one speedily, easily, and reliably. In this manner, a surgical operation time can be reduced, and a patient's pain can be reduced.

In addition, a compression member is eliminated, and one end of the manipulating wire is retracted, whereby the clips can be continuously protruded and ligated. In this manner, a construction can be simplified, and thus, the introducing tube can be reduced in diameter.

Further, the curvature radius of the return portion of the manipulating wire is increased by a holding element provided at the distal end portion of the introducing tube, whereby the traction force quantity of the manipulating wire can be reduced.

In the embodiments each, although three clips have been mounted in the introducing tube, four or more clips may be mounted.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A living tissue ligating apparatus comprising:
an introducing tube capable of being inserted into a living body cavity;
first and second tube channels provided in the introducing tube and extending in an axial direction thereof;
first and second clips for ligating living tissues, the clips being arranged in series in the first tube channel; and
first and second manipulating wires movably inserted into the first and second tube channels, respectively, the first and second manipulating wires being respectively engaged with said first and second clips.

2. An apparatus according to claim 1, wherein at least one further manipulating wire is engaged with at least one further clip which is inserted into the first tube channel.

3. An apparatus according to claim 1, wherein said first and second clips each have a proximal end portion, and a pinch section is formed at a distal end of an arm section which extends from the proximal end portion, thereby imparting expanding/opening properties.

4. An apparatus according to claim 3, wherein there is provided a clip tightening ring engagingly mounted on an arm section of the first and second clips, thereby closing a pinch section of the first and second clips.

5. An apparatus according to claim 4, wherein, at the clip tightening ring, there is provided engaging means for, when said first and second clips and clip tightening ring are protruded frontally of the introducing tube, engaging the introducing tube and clip tightening tube with each other, and inhibiting the clip tightening ring from being housed again in the introducing tube.

6. An apparatus according to claim 5, wherein a movably-inserted compression member is provided in close proximity to the clip tightening ring arranged at the most proximal end portion of the introducing tube.

7. An apparatus according to claim 5, wherein the tube channel in which said clips and clip tightening ring are mounted is shaped so as not to come into contact with means for engaging the clip tightening ring.

8. An apparatus according to claim 1, wherein a communicating channel which communicates the tube channel which houses said clips with the tube channel into which the manipulating wire is inserted is provided in at least a region in which the clips are arranged.

9. An apparatus according to claim 1, wherein a part of the sectional shape of the tube channel which houses said clips and a part of the sectional shape of the tube channel into which the manipulating wire is inserted are superimposed, whereby a communicating channel is formed.

10. A living tissue ligating apparatus comprising:
an introducing tube capable of being inserted into a living body cavity;
a manipulating wire movably inserted into the introducing tube; and
at least two clips for ligating living tissues, the clips being arranged in the introducing tube, wherein the manipulating wire has a loop section in close proximity to a distal end of the introducing tube, first and second sections extending from the loop section to a proximal end portion of the introducing tube, the at least two clips are securely fixed to the first section, and retracting means is provided to a proximal end side of the second section.

11. An apparatus according to claim 10, wherein said at least two clips each have a proximal end portion, a pinch section is formed at a distal end of an arm section which extends from the proximal end portion, and opening/expanding properties are imparted.

12. An apparatus according to claim 11, wherein there is provided a clip tightening ring engagingly mounted on an arm section of the at least two clips, thereby closing the pinch section of the at least two clips.

13. An apparatus according to claim 12, wherein, at the clip tightening ring, there is provided engaging means for, when said at least two clips and clip tightening ring are protruded frontally of the introducing tube, engaging the introducing tube and clip tightening tube with each other, and inhibiting the clip tightening ring from being housed again in the introducing tube.

14. An apparatus according to claim 10, wherein said at least two clips and manipulating wire are connected with each other via a connecting wire, and the connecting wire breaks with a predetermined force quantity when a force of closing the at least two clips is applied.

15. An apparatus according to claim 10, wherein a holding element engaged with a loop section of the manipulating wire is provided in close proximity to a distal end of said introducing tube.

16. An apparatus according to claim 15, wherein a distal opening portion of the tube channel which houses said at least two clips is provided to be more proximal than a distal end opening portion of the tube channel into which the manipulating wire is inserted, and a portion of the engagement between the manipulating wire and holding element is provided in a distal end extension of the tube channel which houses the at least two clips.

17. A ligating apparatus for ligating tissue in the body of a patient, the ligating apparatus comprising:
an introducing tube for insertion into a body cavity of the patient, said introducing tube having first and second channel regions formed therein so as to extend next to each other in a longitudinal direction thereof;
a plurality of clips received in the introducing tube one behind the other in the longitudinal direction; and
manipulating wire means movably extending in the introducing tube for applying the plurality of clips through exertion of a pulling force on the manipulating wire means, the manipulating wire means comprises a plurality of separately operable manipulating wires each engaged with one of the plurality of clips;
wherein the plurality of clips are housed in the first channel region, and an advancing wire portion extends in the first channel region and a returning wire portion extends through the second channel region.

* * * * *